US010556952B2

(12) United States Patent
Davis et al.

(10) Patent No.: US 10,556,952 B2
(45) Date of Patent: Feb. 11, 2020

(54) HEAVY CHAIN CONSTANT REGIONS WITH REDUCED BINDING TO FC GAMMA RECEPTORS

(71) Applicant: Regeneron Pharmaceuticals, Inc., Tarrytown, NY (US)

(72) Inventors: Samuel Davis, New York, NY (US); Eric Smith, New York, NY (US); Tong Zhang, Fort Lee, NJ (US); Supriya Patel, Mamaroneck, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 101 days.

(21) Appl. No.: 15/562,881

(22) PCT Filed: Mar. 30, 2016

(86) PCT No.: PCT/US2016/025051
§ 371 (c)(1),
(2) Date: Sep. 28, 2017

(87) PCT Pub. No.: WO2016/161010
PCT Pub. Date: Oct. 6, 2016

(65) Prior Publication Data

US 2018/0282411 A1 Oct. 4, 2018

Related U.S. Application Data

(60) Provisional application No. 62/140,350, filed on Mar. 30, 2015.

(51) Int. Cl.
*C07K 16/28* (2006.01)

(52) U.S. Cl.
CPC ...... *C07K 16/2809* (2013.01); *C07K 16/2887* (2013.01); *C07K 2317/31* (2013.01); *C07K 2317/526* (2013.01); *C07K 2317/53* (2013.01); *C07K 2317/71* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,624,821 | A | 4/1997 | Winter et al. |
| 5,648,260 | A | 7/1997 | Winter et al. |
| 6,180,377 | B1 | 1/2001 | Morgan et al. |
| 7,396,917 | B2 | 7/2008 | Bowdish et al. |
| 7,563,441 | B2 | 7/2009 | Graus et al. |
| 7,597,889 | B1 | 10/2009 | Armour et al. |
| 7,608,260 | B2 | 10/2009 | Schenerman et al. |
| 7,700,097 | B2 | 4/2010 | Braskawsky et al. |
| 7,700,099 | B2 | 4/2010 | Strohl |
| 7,728,114 | B2 | 6/2010 | Mach et al. |
| 7,820,166 | B2 | 10/2010 | Lanzavecchia et al. |
| 7,824,684 | B2 | 11/2010 | Graus et al. |
| 7,867,491 | B2 | 1/2011 | Yang et al. |
| 7,960,512 | B2 | 6/2011 | Stavenhagen et al. |
| 8,075,884 | B2 | 12/2011 | Bowdish et al. |
| 8,084,026 | B2 | 12/2011 | Glaser et al. |
| 8,153,583 | B2 | 4/2012 | Carton et al. |
| 8,236,314 | B2 | 8/2012 | Kai et al. |
| 8,268,972 | B2 | 9/2012 | Whitfeld et al. |
| 8,383,109 | B2 | 2/2013 | Lazar et al. |
| 8,409,568 | B2 | 4/2013 | Gao et al. |
| 8,961,967 | B2 | 2/2015 | Strohl et al. |
| 9,359,437 | B2 | 6/2016 | Davis et al. |
| 10,106,610 | B2 | 10/2018 | Davis et al. |

(Continued)

FOREIGN PATENT DOCUMENTS

| | | | |
|---|---|---|---|
| EP | 0327378 | B1 | 12/1996 |
| EP | 2918604 | A1 | 9/2015 |

(Continued)

OTHER PUBLICATIONS

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.com/content/11/1/1160>].
U.S. Appl. No. 15/147,791, Notice of Allowance dated Mar. 1, 2018.
U.S. Appl. No. 15/147,791, Notice of Allowance dated Jun. 12, 2018.
U.S. Appl. No. 61/759,578, filed Feb. 1, 2013, Expired, 8550P1.
U.S. Appl. No. 14/170,166, filed Jan. 31, 2014, U.S. Pat. No. 9,359,437, Issued, 8550-US.
U.S. Appl. No. 15/147,791, filed May 5, 2016, U.S. Pat. No. 10,106,610, Issued, 8550US02.
PCT/U52014/014175, filed Jan. 31, 2014, WO 2014/022540, Expired, 8550-WO.
U.S. Appl. No. 16/128,907, filed Sep. 12, 2018, Pending, 8550US03.

(Continued)

*Primary Examiner* — Nelson B Moseley, II
(74) *Attorney, Agent, or Firm* — Schwabe, Williamson & Wyatt PC; Kristan Lansbery

(57) ABSTRACT

The invention provides antibody heavy chain constant regions with a hinge region modified to reduce binding to Fcγ receptors. The modification occurs within positions 233-236 by replacement of natural residues by glycine(s) and/or deletion(s). Such modifications can reduce binding of an antibody bearing such a constant region to Fcγ receptors to background levels. The constant regions can be incorporated into any format of antibody or Fc fusion protein. Such antibodies or fusion proteins can be used in methods of treatment, particularly those in which the mechanisms of action of the antibody or Fc fusion protein is not primarily or at all dependent on effector functions, as is the case when an antibody inhibits a receptor-ligand interaction or agonizes a receptor.

24 Claims, 18 Drawing Sheets

Specification includes a Sequence Listing.

(56) References Cited

U.S. PATENT DOCUMENTS

| | | | |
|---|---|---|---|
| 2005/0037000 | A1 | 2/2005 | Stavenhagen et al. |
| 2005/0226876 | A1 | 10/2005 | Graus et al. |
| 2005/0244403 | A1 | 11/2005 | Lazar et al. |
| 2007/0009523 | A1 | 1/2007 | Presta |
| 2007/0041972 | A1 | 2/2007 | Rother et al. |
| 2009/0117133 | A1 | 5/2009 | Arnason et al. |
| 2009/0162901 | A1 | 6/2009 | Chen et al. |
| 2009/0252729 | A1 | 10/2009 | Farrington et al. |
| 2010/0105874 | A1 | 4/2010 | Schuurman et al. |
| 2010/0166749 | A1 | 7/2010 | Presta |
| 2010/0267934 | A1 | 10/2010 | Winkel et al. |
| 2010/0298542 | A1 | 11/2010 | Igawa et al. |
| 2010/0325744 | A1 | 12/2010 | Schuurman et al. |
| 2010/0331527 | A1 | 12/2010 | Davis et al. |
| 2011/0077383 | A1 | 3/2011 | Dall'Acqua et al. |
| 2011/0212087 | A1 | 9/2011 | Strohl et al. |
| 2011/0245473 | A1 | 10/2011 | Igawa et al. |
| 2011/0263830 | A1 | 10/2011 | Goetsch et al. |
| 2011/0293607 | A1 | 12/2011 | Labrijn et al. |
| 2012/0065379 | A1 | 3/2012 | Igawa et al. |
| 2012/0071634 | A1 | 3/2012 | Igawa et al. |
| 2012/0100140 | A1 | 4/2012 | Reyes et al. |
| 2012/0189643 | A1 | 7/2012 | Carton et al. |
| 2012/0225058 | A1 | 9/2012 | Lazar et al. |
| 2012/0237515 | A1 | 9/2012 | Bell et al. |
| 2012/0238729 | A1 | 9/2012 | Kuramochi et al. |
| 2012/0251531 | A1 | 10/2012 | Baehner et al. |
| 2012/0276096 | A1 | 11/2012 | Yang et al. |
| 2012/0276097 | A1 | 11/2012 | Yang et al. |
| 2013/0011386 | A1 | 1/2013 | Brezski et al. |
| 2013/0101581 | A1 | 4/2013 | Kuramochi et al. |
| 2013/0108623 | A1 | 5/2013 | D'Angelo et al. |
| 2013/0129723 | A1 | 5/2013 | Blankenship et al. |
| 2013/0251707 | A1 | 9/2013 | Kontermann et al. |
| 2014/0088295 | A1 | 3/2014 | Smith et al. |
| 2014/0112914 | A1 | 4/2014 | Nezu et al. |
| 2014/0120581 | A1 | 5/2014 | Niwa et al. |
| 2015/0166661 | A1 | 6/2015 | Chen et al. |
| 2015/0203579 | A1 | 7/2015 | Papadopoulos et al. |
| 2016/0168247 | A1 | 6/2016 | Van Den Brink et al. |
| 2016/0347839 | A1 | 12/2016 | David et al. |
| 2017/0008951 | A1 | 1/2017 | Block et al. |
| 2018/0303953 | A1 | 10/2018 | Van Berkel et al. |

FOREIGN PATENT DOCUMENTS

| | | | | |
|---|---|---|---|---|
| WO | 97/028267 A1 | 8/1997 | | |
| WO | 99/043713 A1 | 9/1999 | | |
| WO | 99/058572 A1 | 11/1999 | | |
| WO | 00/042072 A2 | 7/2000 | | |
| WO | 03/026490 A2 | 4/2003 | | |
| WO | 10/054212 A1 | 5/2010 | | |
| WO | 10/063785 A2 | 6/2010 | | |
| WO | 10/085682 A2 | 7/2010 | | |
| WO | 11/137362 A1 | 11/2011 | | |
| WO | 12/022982 A2 | 2/2012 | | |
| WO | 12/035141 A1 | 3/2012 | | |
| WO | 12/087746 A1 | 6/2012 | | |
| WO | 2012/073985 A1 | 6/2012 | | |
| WO | 13/012733 A1 | 1/2013 | | |
| WO | 13/026839 A1 | 2/2013 | | |
| WO | 13/112986 A1 | 8/2013 | | |
| WO | 13/184761 A1 | 12/2013 | | |
| WO | 14/012085 A2 | 1/2014 | | |
| WO | 14/022540 A1 | 2/2014 | | |
| WO | 14/047231 A1 | 3/2014 | | |
| WO | 14/051433 A1 | 4/2014 | | |
| WO | 14/056783 A1 | 4/2014 | | |
| WO | 14/121087 A1 | 8/2014 | | |
| WO | WO 2014/121087 * | 8/2014 | ............ | C07K 16/28 |
| WO | 2015-006749 A2 | 1/2015 | | |
| WO | 15/091738 A1 | 6/2015 | | |
| WO | 15/143079 A1 | 9/2015 | | |
| WO | 16/161010 A2 | 10/2016 | | |
| WO | 17/053856 A1 | 3/2017 | | |

OTHER PUBLICATIONS

U.S. Appl. No. 61/704,029, filed Sep. 21, 2012, Expired, 9250P1.
U.S. Appl. No. 61/753,461, filed Jan. 17, 2013, Expired, 9250P2.
U.S. Appl. No. 61/763,110, filed Feb. 11, 2013, Expired, 9250P3.
U.S. Appl. No. 61/827,098, filed May 24, 2013, Expired, 9250P4.
U.S. Appl. No. 14/031,075, filed Sep. 19, 2013, U.S. Pat. No. 9,657,102, Issued, 9250-US.
U.S. Appl. No. 15/489,666, filed Apr. 17, 2017, US 2017-0320948, Pending, 9250US02.
PCT/U52013/060511, filed Sep. 19, 2013, WO 2014/047231, Expired, 9250-WO.
U.S. Appl. No. 15/934,447, filed Mar. 23, 2018, US 2018-0215823, Pending, 9250US03.
U.S. Appl. No. 61/955,663, filed Mar. 19, 2014, Expired, A0015P1.
U.S. Appl. No. 61/981,641, filed Apr. 18, 2014, Expired, A0015P2.
U.S. Appl. No. 62/007,385, filed Jun. 3, 2014, Expired, A0015P3.
U.S. Appl. No. 62/033,460, filed Aug. 5, 2014, Expired, A0015P4.
U.S. Appl. No. 14/661,334, filed Mar. 18, 2015, US 2015-0266966, Pending, A0015US01.
PCT/U52015/021322, filed Mar. 18, 2015, WO 2015/143079, Expired, A0015WO01.
U.S. Appl. No. 62/080,716, filed Nov. 17, 2014, Expired, 10162P1-US.
U.S. Appl. No. 62/160,788, filed May 13, 2015, Expired, 10162P2-US.
PCT/U52015/061139, filed Nov. 17, 2015, WO 2016/081490, Pending, 10162WO01.
U.S. Appl. No. 15/527,002, filed Nov. 17, 2015, US 2018-0194841, Pending, 10162US01.
U.S. Appl. No. 62/306,031, filed Mar. 9, 2016, Expired, 10241P1-US.
U.S. Appl. No. 15/386,443, filed Dec. 21, 2016, US 2017-0174781, Pending, 10241US01.
PCT/U52016/068003, filed Dec. 21, 2016, WO 2017/112762, Pending, 10241WO01.
U.S. Appl. No. 62/140,350, filed Mar. 30, 2015, Expired, 10140P1-US.
PCT/U52016/025051, filed Mar. 30, 2016, WO 2016/161010, Pending, 10140WO01.
U.S. Appl. No. 62/222,605, filed Sep. 23, 2015, Expired, 10151P1-US.
PCT/U52016/053525, filed Sep. 23, 2016, WO 2017/053856, Pending, 10151WO01.
U.S. Appl. No. 15/780,504, filed Sep. 23, 2016, Pending, 10151US01.
U.S. Appl. No. 14/170,166, Requirement for Restriction/Election dated Jul. 27, 2015.
WIPO Application No. PCT/US2014/014175, PCT International Search Report and Written Opinion of the International Searching Authority dated Jul. 9, 2014.
WIPO Application No. PCT/US2014/014175, PCT International Preliminary Report on Patentability dated Aug. 13, 2015.
"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605 pdf >].
"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].
Greenwood et al., "Structural Motifs Involved in Human IGG Antibody Effector Functions," Eur. J. Immunology, 23(5):1098-1104, (1993).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Canfield et al., "The Binding Affinity of Human IgG for Its High Affinity Fc Receptor is Determined by Multiple Amino Acids in the CH2 Domain and is Modulated by the Hinge Region," J. Exp. Med., 173(6):1483-1491, (1991).
Natsume et al., "Engineered Antibodies of IgG1IIgG3 Mixed Isotype with Enhanced Cytotoxic Activities," Cancer Research, 68:(10):3863-3872, (2008).

(56) References Cited

OTHER PUBLICATIONS

Chappel et al., "Identification of the FC-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Aalberse et al., "IgG4 breaking the rules," Immunology, 105(1):9-19, (2002).
Rother et al., "Discovery and development of the complement inhibitor eculizumab for the treatment of paroxysmal nocturnal hemoglobinuna," Nature Biotechnology, 25(11):1256-1264, (2007).
Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).
Salfeld, "Isotype selection in antibody engineering," Nature Biotechnology, 25(12):1369-1372, (2007).
Vafa, et al., "An engineered Fc variant of an IgG eliminates all immune effector functions via structural perturbations", 65:114-126, (2014). (Published online Jul. 17, 2013).
Patel et al., "IGG subclass variation of a monoclonal antibody binding to human Fc-gamma receptors", American Journal of Biochemistry and Biotechnology, 9(3):206-218, (2013).
Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).
An et al., "IgG2m4, an engineered antibody isotype with reduced Fc function," Landes Bioscience, 1(6):572-579, (2009).
Armour et al., "Differential binding to human FcyRIIa and FcyRIIb receptors by human IgG wildtype and mutant antibodies," Molecular Immunology, 40:585-593, (2003).
Armour et al., "Recombinant human IgG molecules lacking Fcy receptor I binding and monocyte triggering activities", J. Immunol., 29:2613-2624, (1999).
Bloom et al., "Intrachain disulfide bond in the core hinge region of human IgG4," Protein Science, 6:407-415, (1997).
Brekke et al., "The structural requirements for complement activation by IgG: does it hinge on the hinge?" Today, 16(2):85-90, (1995).
Chappel et al., "Identification of a Secondary FcyRI Binding Site within a Genetically Engineered Human IgG," Journal of Biological Chemistry, 268(33): 25124-25131, (1993).
Clark, "IgG Effector Mechanisms," Chem Immunol. Basel, Karger, 65:88-110, (1997).
Dall'Acqua et al., "Modulation of the Effector Functions of a Human IgG1 through Engineering of Its Hinge Region," Journal of Immunology, 177:1129-1138, (2006).
Dangl et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on IgG", Nature, 332:563-564, (1988).
Gergely et al., "The two binding-site models of human IgG binding Fcy receptors", The FASEB Journal, 4:3275-3283, (1990).
Jacobsen et al., "Molecular and Functional Characterization of Cynomolgus Monkey IgG Subclasses," Journal Immunology, 186:341-349, (2011).
Jefferis et al., "Recognition sites on human IgG for Fcy receptors: the role of glycosylation," Immunology Letters, 44:111-117, (1995).
Jefferis et al., "Interaction sites on human IgG-Fc for FcyR: current models", Immunology Letters, 82:57-65, (2002).
Labrijn et al., "When binding is enough: nonactivating antibody formats", Current Opinion in Immunology, 20:479-485, (2008).
Lund et al., "Human FcyRI and FcyRII Interact with Distinct but Overlapping Sites on Human IgG", Journal of Immunology, 147(8):2657-2662, (1991).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgG1 anti-HLA-DR is necessary for Gig, FcyRI and FcyRII binding," Immunology, 86:319-324, (1995).
Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Oganesyan et al., "Structural characterization of a human Fc fragment engineered for lack of effector functions," Acta Crystallographica Section D Biological Crystallography, D64:700-704, (2008).
Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).
Reddy et al., "Elimination of Fc Receptor-Dependent Effector Functions of a Modified IgG4 Monoclonal Antibody to Human CD4," Journal of Immunology, 164:1925-1933, (2000).
Roux et al., "Flexibility of Human IgG Subclasses," Journal of Immunology, 159:3372-3382, (1997).
Sarmay et al., "Mapping and Comparison of the Interaction Sites on the Fc Region of IgG Responsible for Triggering Antibody Dependent Cellular Cytotoxicity (ADCC) through Different Types of Human Fcy Receptor," Molecular Immunology, 29(5):633-639, (1992).
Sathish et al., "Challenges and approaches for the development of safer immunomodulatory biologics," Nature Reviews Drug Discovery, 12:306-324, (2013).
Sensel et al., "Amino Acid Differences in the N-Terminus of CH2 Influence the Relative Abilities of IgG2 and IgG3 to Activate Complement", Molecular Immunology, 34(14):1019-1029, (1997).
Siberil et al., "Molecular aspects of human FcyR interactions with IgG: Functional and therapeutic consequences," Immunology Letters, 106:111-118, (2006).
Stevenson, "Chemical Engineering at the Antibody Hinge," Chem Immunol. Basel, Karger, 65:57-72, (1997).
Tan et al., "Influence of the hinge region on complement activation, C1q binding, and segmental flexibility in chimeric human immunoglobulins,", Proc. Natl. Acad. Sci. USA, 87:162-166, (1990).
Ward et al., "The effector functions of immunoglobulins: implications for therapy," Therapeutic Immunology, 2:77-94, (1995).
Wypych et al., "Human IgG2 Antibodies Display Disulfide-mediated Structural Isoforms," Journal of Biological Chemistry, 283(23):16194-16205, (2008).
U.S. Appl. No. 14/170,166, Non-Final Office Action dated Dec. 21, 2015.
U.S. Appl. No. 14/170,166, Notice of Allowance dated Apr. 11, 2016.
Lum et al., "CD2O-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Published online Sep. 23, 2013].
Sun et al., "Anti-CD20/CD3 T cell—dependent bispecific antibody for the treatment of B cell malignancies," Science Translational Medicine, 7(287):287ra70, 10 pages, (2015).
WIPO Application No. PCT/US2016/025051, PCT International Search Report and Written Opinion of the International Searching Authority dated Oct. 12, 2016.
Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).
Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).

(56) References Cited

OTHER PUBLICATIONS

Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).

Vidarsson et al., "IgG Subclasses and Allotypes: From Structure to Effector Functions," Frontiers in Immunology, vol. 5, Article 520, 18 pages, doi: 10.3389/fimmu.2014.00520, (2014).

WIPO Application No. PCT/US2016/053525, PCT International Search Report and Written Opinion of the International Searching Authority dated Mar. 8, 2017.

Wu et al., "Fab-based bispecific antibody formats with robust biophysical properties and biological activity," MABS, pp. 470-482, ISSN: 1942-0870, (2015).

Cao et al., "Multiformat T-Cell-Engaging Bispecific Antibodies Targeting Human Breast Cancers," Angew Chem Int Ed Engl, 54(24):7022-7027, doi: 10.1002/anie.201500799, (2015).

Jung et al., "Target Cell-Induced T Cell Activation with Bi- and Trispecific Antibody Fragments", EurJ Immunol, vol. 21, pp. 2431-2435, doi: 10.1002/EJI.1830211020, (1991).

Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).

Schaefer et al., "Immunoglobulin domain crossover as a generic approach for the production of bispecific IgG antibodies," PNAS, 108(27):11187-11192, doi: 10.1073/pnas.1019002108, (2011).

Li et al., "A Novel Bispecific Antibody, S-Fab, Induces Potent Cancer Cell Killing," J Immunother, 38(9):350-356, doi: 10.1097/CJI.0000000000000099, (2015).

Almagro et al., "Humanization of antibodies," Front Biosci, vol. 13, pp. 1619-163, (2008).

Baeuerle et al., "Bispecific T-cell engaging antibodies for cancer therapy," Cancer Res, 69(12):4941-4944, doi: 10.1158/0008-5472.CAN-09-0547, (2009).

Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).

Buhmann et al., "Immunotherapy of recurrent B-cell malignancies after alto-SCT with Bi20 (FBTA05), a trifunctional anti-CD3 x anti-CD20 antibody and donor lymphocyte infusion," Bone Marrow Transplantation, 43:383-397, (2009).

Strop et al., "Generating Bispecific Human IgG1 and IgG2 Antibodies from Any Antibody Pair", J. Mol. Biol., 420(3):204-219, (2012).

Schuster et al., "Immunotherapy with the trifunctional anti-CD20 x anti-CD3 antibody FBTA05 Lymphomun) in paediatric high-risk patients with recurrent CD20-positive B cell malignancies," British Journal of Haematolgy, vol. 169 (No. 1): (Apr. 11, 2015); pp. 90-102.

Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].

Anonymous, "Study of REGN2810 and REGN1979 in Patientcs with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country= UnitedStates&start=20&state=Maryland&conditions=lymphoma&id=207048402254>].

Advani et al., "New immune strategies for the treatment of acute pymphoblastic leukemia: antiobodies and chimeric antigen receptors," Hematology, vol. 2013 (No. 1): (Dec. 1, 2013).

U.S. Appl. No. 15/147,791, Non-Final Office Action dated Sep. 27, 2017.

Becker et al., "Evaluation of a combinatorial cell engineering approach to overcome apoptotic effects in XBP-1(s) expressing cells," Journal of Biotechnology, vol. 164:198-206, (2010).

Bargou et al., "Tumor egression in Cancer Patients by Very Low Doses of a T Cell-Engaging Antibody," Science Magazine, vol. 321: 974-977, (2008).

Damschroder et al., "Analysis of human and primate CD2 molecules by protein sequence and epitope mapping with anti-human CD2 antibodies," Molecular Immunology, vol. 41:985-1000, (2004).

Grubb, "Human immunoglobulin allotypes and Mendelian polymorphisma of the human immunoglobulin genes," Oss CJ, Regenmortel MHV (eds): Immunochemistry, New York, Dekker; pp. 47-68 (1994).

Harlow et al., Antibodies, A Laboratory Manual, Cold Spring Harbor Laboratory; (1998) pp. 37-47.

Haso et al., "Anti-CD22-chimeric antigen receptors targeting B-cell precursor acute lymphoglastic leukemia," Blood, vol. 121 (No. 7):1165-1174, Feb. 14, 2013.

Kapur et al., "IgG-effector functions: The Good, The Bad and The Ugly," El Sevier, vol. 160:139-144, (2014).

Kohnke et al., "Increase of PD-L1 expressing B-precursor ALL cells in a patient resistant to the CD19/CD3-bispecific T cell engager antibody blinatumomab," Journal of Hematology & Oncology, vol. 8 (No. 111): 5 pages, (2015).

Kumar et al., "Expression of CD20 in B Cell Precursor Acute Lymphoblastic Leukemia," Indian J Hematol Blood Transfus, vol. 30 (No. 1):16-18, (2014).

NCBI MedGen 44126 definition for "Pre-B Acute Lumphoblastic Leukemia"; retrieved from the Internet on Dec. 11, 2018, pp. 1-4, available at <https://www.ncbi.nlm.nih.gov/medgen/44126/> (2018).

Ontology Lookup Service, EFO 0000220, "acute lumphoblastic leukemia", retrieved from the Internet on Dec. 11, 2018, pp. 1-6, available at <https://www.ebi.ac.uk/ols/ontologies/efo/terms?short_form=EF0_0000220> (2018).

Ruf et al., "Induction of a long-lasting antitumor immunity by a trifunctional bispecific antibody," Blood Journal, vol. 98, No. 9: 2526-2534, (2001).

Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).

Thomas et al., "Chemoimmunotherapy with a Modified Hyper-CVAD and Rituximab Regimen Improves Outcome in De Novo Philadelphia Crhomosome-Negative Precursor B-Lineage Acute Lumphoblastic Leukemia," Journal of Clinical Oncology, vol. 28 (No. 24):3880-3889; Aug. 20, 2010.

Topp et al., "Safety and activity of blinatumomab for adult patients with relapsed or refractory B-precursor acute lymphoblastic leukaemia: a multicentre, single-arm, phase 2 study," Publication, vol. 16:57-66, (Jan. 2015).

Tsai et al., "Regulation of CD20 in Rituximab-Resistant Cell Lines and B-cell Non-Hodgkin Lymphoma," Clinical Cancer Research, vol. 18(No. 4):1039-1050, (2012).

Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).

* cited by examiner

FIG. 1

Corresponding amino acid numbering conventions for hinge regions: hIgG1, hIgG2 and hIgG4

| | Hinge | | | | | | | | | | | | | | | Hinge encoded by CH2 exon | | | | | |
|---|---|---|---|---|---|---|---|---|---|---|---|---|---|---|---|---|---|---|---|---|---|
| hIgG1 wt | E | P | K | S | C | D | K | T | H | T | C | P | P | C | P | A | P | E | L | L | G |
| hIgG1 EU | 216 | 217 | 218 | 219 | 220 | 221 | 222 | 223 | 224 | 225 | 226 | 227 | 228 | 229 | 230 | 231 | 232 | 233 | 234 | 235 | 236 |
| hIgG1 Kabat | 226 | 227 | 228 | 232[a] 229[b] | 233[a] 230[b] | 234[a] 232[b] | 235 | 236 | 237 | 238 | 239 | 240 | 241 | 242 | 243 | 244 | 245 | 246 | 247 | 248 | 249 |
| hIgG1 IMGT | 1 | 2 | 3 | 4 | 5 | 6 | 7 | 8 | 9 | 10 | 11 | 12 | 13 | 14 | 15 | 1.6 | 1.5 | 1.4 | 1.3 | 1.2 | 1.1 |
| hIgG2 wt | E | R | K | C | C | -- | V | -- | E | -- | C | P | P | C | P | A | P | P | V | A | -- |
| hIgG2 EU | 216 | 217 | 218 | 219[a] 221[b] | 220[a] -[b] | | 222 | | 224 | | 226 | 227 | 228 | 229 | 230 | 231[a] | 232[a] | 233[a] | 234[a] | 235[a] | 236[a] |
| hIgG2 Kabat | 226 | 227 | 228 | 232 | 233 | | 235 | | 237 | | 239 | 240 | 241 | 242 | 243 | 244 | 245 | 246 | 247 | 248 | 249 |
| hIgG2 IMGT | 1 | 2 | 3 | 4 | 5 | | 6 | | 7 | | 8 | 9 | 10 | 11 | 12 | - | - | - | - | - | |
| hIgG4 wt | E | S | K | Y | G | -- | -- | -- | P | P | C | P | S | C | P | A | P | E | F | L | G |
| hIgG4 EU | 216 | 217 | 218 | -[a] 219[b] | -[a] 220[b] | | | | 224 | 225 | 226 | 227 | 228 | 229 | 230 | 231[a] | 232[a] | 233[a] | 234[a] | 235[a] | 236[a] |
| hIgG4 Kabat | 226 | 227 | 228 | 229 | 230 | | | | 237 | 238 | 239 | 240 | 241 | 242 | 243 | 244 | 245 | 246 | 247 | 248 | 249 |
| hIgG4 IMGT | 1 | 2 | 3 | 4 | 5 | | | | 6 | 7 | 8 | 9 | 10 | 11 | 12 | - | - | - | - | - | - |

wt = wild-type

- means no corresponding number reported

-- means no corresponding amino acid

[a] numbering according to the last updated IMGT Scientific Chart (IMGT®, the international ImMunoGeneTics information system®, http://www.imgt.org/IMGTScientificChart/Numbering/Hu_IGHGnber.html, created: 17 May 2001, last updated:10 Jan 2013)

[b] numbering according to EU index as reported in Kabat, E.A. et al. Sequences of Proteins of Immunological interest. 5th ed. US Department of Health and Human Services, NIH publication No. 91-3242 (1991)

FIG. 2

```
        10         20         30         40         50         60
ASTKGPSVFP LAPSSKSTSG GTAALGCLVK DYFPEPVTVS WNSGALTSGV HTFPAVLQSS

                                  <-- CH1  Hinge-->               CH2-->
        70         80         90        100        110        120
GLYSLSSVVT VPSSSLGTQT YICNVNHKPS NTKVDKKVEP KSCDKTHTCP PCPAPELLGG

       130        140        150        160        170        180
PSVFLFPPKP KDTLMISRTP EVTCVVVDVS HEDPEVKFNW YVDGVEVHNA KTKPREEQYN

                                             CH3-->
       190        200        210        220        230        240
STYRVVSVLT VLHQDWLNGK EYKCKVSNKA LPAPIEKTIS KAKGQPREPQ VYTLPPSRDE

       250        260        270        280        290        300
LTKNQVSLTC LVKGFYPSDI AVEWESNGQP ENNYKTTPPV LDSDGSFFLY SKLTVDKSRW

       310        320        330
QQGNVFSCSV MHEALHNHYT QKSLSLSPGK
```

Human IGHG1 heavy chain constant region
UniProtKB/Swiss-Prot Accn. No. P01857
(SEQ ID NO:13)

FIG. 3

```
        10         20         30         40         50         60
ASTKGPSVFP LAPCSRSTSE STAALGCLVK DYFPEPVTVS WNSGALTSGV HTFPAVLQSS

                                   ←CH1  Hinge→              CH2→
        70         80         90        100        110        120
GLYSLSSVVT VPSSNFGTQT YTCNVDHKPS NTKVDKTVER KCCVECPPCP APPVAGPSVF

       130        140        150        160        170        180
LFPPKPKDTL MISRTPEVTC VVVDVSHEDP EVQFNWYVDG VEVHNAKTKP REEQFNSTFR

                                            CH3→
       190        200        210        220        230        240
VVSVLTVVHQ DWLNGKEYKC KVSNKGLPAP IEKTISKTKG QPREPQVYTL PPSREEMTKN

       250        260        270        280        290        300
QVSLTCLVKG FYPSDISVEW ESNGQPENNY KTTPPMLDSD GSFFLYSKLT VDKSRWQQGN

       310        320
VFSCSVMHEA LHNHYTQKSL SLSPGK
```

Human IGHG2 heavy chain constant region
UniProtKB/Swiss-Prot Accn. No. P01859
(SEQ ID NO:14)

FIG. 4

```
        10         20         30         40         50         60
ASTKGPSVFP LAPCSRSTSE STAALGCLVK DYFPEPVTVS WNSGALTSGV HTFPAVLQSS

                                 ← CH1 Hinge→                 CH2→
        70         80         90        100        110        120
GLYSLSSVVT VPSSSLGTKT YTCNVDHKPS NTKVDKRVES KYGPPCPSCP APEFLGGPSV

       130        140        150        160        170        180
FLFPPKPKDT LMISRTPEVT CVVVDVSQED PEVQFNWYVD GVEVHNAKTK PREEQFNSTY

                                            CH3→
       190        200        210        220        230        240
RVVSVLTVLH QDWLNGKEYK CKVSNKGLPS SIEKTISKAK GQPREPQVYT LPPSQEEMTK

       250        260        270        280        290        300
NQVSLTCLVK GFYPSDIAVE WESNGQPENN YKTTPPVLDS DGSFFLYSRL TVDKSRWQEG

       310        320
NVFSCSVMHE ALHNHYTQKS LSLSLGK
```

Human IGHG4 heavy chain constant region
UniProtKB/Swiss-Prot Accn. No. P01861
(SEQ ID NO:15)

FIG. 6

| mAb designation | Target arm | Construct description | hFcRγI captured (RU) | mAb -5uM bound (RU) | ka | kd | KD | t1/2 (min) | Rmax |
|---|---|---|---|---|---|---|---|---|---|
| 9F7_VH_IgG4 _GGG-(233-236) | aCD3(9F7) bivalent | lower hinge of IgG4 at 233-236 replaced with GGG (and S228P) | 171 | 1 | NB | NB | NB | NB | NB |
| 9F7_VH_IgG4 _GG--(233-236) | aCD3(9F7) bivalent | lower hinge of IgG4 at 233-236 replaced with GG (and S228P) | 171 | -1 | NB | NB | NB | NB | NB |
| 9F7_VH_IgG4_G---(233-236) | aCD3(9F7) bivalent | lower hinge of IgG4 at 233-236 replaced with G (and S228P) | 170 | 0 | NB | NB | NB | NB | NB |
| 9F7_VH_IgG4_No_G(233-236) | aCD3(9F7) bivalent | lower hinge of IgG4 at 233-236 deleted (and S228P) | 169 | -1 | NB | NB | NB | NB | NB |
| Control Ab A (Lot- L2) 9F7_VH_IgG4 | aCD3(9F7) bivalent | wild type IgG4 Fc (except CH3 mutation 435R and 436F) | 168 | 112 | 8.20E+05 | 2.30E-03 | 2.81E-09 | 5 | 94 |
| Control Ab D (Lot- L5) 9F7_VLx3B9_VH_IgG4_PVA | aCD3(9F7) x aCD20(3B9) | Bispecific mAb with lower hinge of IgG4 at 233-236 replaced with PVA (and S228P) | 169 | 0 | NB | NB | NB | NB | NB |
| Control Ab B (Lot-L2) 9F7_VH_IgG1 | aCD3(9F7) bivalent | wild type IgG1 Fc | 170 | 128 | 7.10E+05 | 8.84E-04 | 1.25E-09 | 13 | 110 |

NB: No binding

FIG. 7

| mAb designation | Target arm | Construct description | hFcRyIIa captured (RU) | mAb -5uM bound (RU) | ka | kd | KD* | t1/2 (min)* | Rmax |
|---|---|---|---|---|---|---|---|---|---|
| 9F7_VH_IgG4 _GGG-(233-236) | aCD3(9F7) bivalent | lower hinge of IgG4 at 233-236 replaced with GGG (and S228P) | 323 | -1 | NB | NB | NB | NB | NB |
| 9F7_VH_IgG4 _GG--(233-236) | aCD3(9F7) bivalent | lower hinge of IgG4 at 233-236 replaced with GG (and S228P) | 319 | -3 | NB | NB | NB | NB | NB |
| 9F7_VH_IgG4_G---(233-236) | aCD3(9F7) bivalent | lower hinge of IgG4 at 233-236 replaced with G (and S228P) | 318 | -2 | NB | NB | NB | NB | NB |
| 9F7_VH_IgG4_No_G(233-236) | aCD3(9F7) bivalent | lower hinge of IgG4 at 233-236 deleted (and S228P) | 320 | 4 | - | - | IC | - | 730 |
| Control Ab A (Lot- L2) 9F7_VH_IgG4 | aCD3(9F7) bivalent | wild type IgG4 Fc (except CH3 mutation 435R and 436F) | 320 | 156 | - | - | 16.8uM | - | 730 |
| Control Ab D (Lot- L5) 9F7_VLx3B9_VH_IgG4_PVA | aCD3(9F7) x aCD20(3B9) | Bispecific mAb with lower hinge of IgG4 at 233-236 replaced with PVA (and S228P) | 320 | 121 | - | - | 22.9uM | - | 730 |
| Control Ab B (Lot-L2) 9F7_VH_IgG1 | aCD3(9F7) bivalent | wild type IgG1 Fc | 321 | 411 | | - | 3.12uM | - | 730 |

*KDs were derived using steady state equilibrium dissociation constant

NB: No binding
IC: value cannot be determined

FIG. 8

| mAb Designation | Target arm | Construct description | hFcRγIIb captured (RU) | mAb -5uM bound (RU) | ka | kd | KD* | t1/2 (min)* | Rmax |
|---|---|---|---|---|---|---|---|---|---|
| 9F7_VH_IgG4 _GGG-(233-236) | aCD3(9F7) bivalent | lower hinge of IgG4 at 233-236 replaced with GGG (and S228P) | 392 | -31 | NB | NB | NB | NB | NB |
| 9F7_VH_IgG4 _GG--(233-236) | aCD3(9F7) bivalent | lower hinge of IgG4 at 233-236 replaced with GG (and S228P) | 390 | -32 | NB | NB | NB | NB | NB |
| 9F7_VH_IgG4_G---(233-236) | aCD3(9F7) bivalent | lower hinge of IgG4 at 233-236 replaced with G (and S228P) | 386 | -31 | NB | NB | NB | NB | NB |
| 9F7_VH_IgG4_No_G(233-236) | aCD3(9F7) bivalent | lower hinge of IgG4 at 233-236 deleted (and S228P) | 387 | -36 | NB | NB | NB | NB | NB |
| Control Ab A (Lot- L2) 9F7_VH_IgG4 | aCD3(9F7) bivalent | wild type IgG4 Fc (except CH3 mutation 435R and 436F) | 388 | 276 | - | - | 2.20uM | - | 393 |
| Control Ab D (Lot- L5) 9F7_VLx3B9_VH_IgG4_PVA | aCD3(9F7) x aCD20(3B9) | Bispecific mAb with lower hinge of IgG4 at 233-236 replaced with PVA (and S228P) | 388 | 17 | - | - | 110uM | - | 393 |
| Control Ab B (Lot-L2) 9F7_VH_IgG1 | aCD3(9F7) bivalent | wild type IgG1 Fc | 387 | 221 | - | - | 4.0uM | - | 393 |

*KDs were derived using steady state equilibrium dissociation constant

NB: No binding

FIG. 9

| mAb Designation | Target arm | Construct description | hFcRγIIIA captured (RU) | mAb -5uM bound (RU) | ka | kd | KD* | t1/2 (min)* | Rmax |
|---|---|---|---|---|---|---|---|---|---|
| 9F7_VH_IgG4 _GGG-(233-236) | aCD3(9F7) bivalent | lower hinge of IgG4 at 233-236 replaced with GGG (and S228P) | 398 | -48 | NB | NB | NB | NB | NB |
| 9F7_VH_IgG4 _GG--(233-236) | aCD3(9F7) bivalent | lower hinge of IgG4 at 233-236 replaced with GG (and S228P) | 380 | -44 | NB | NB | NB | NB | NB |
| 9F7_VH_IgG4_G---(233-236) | aCD3(9F7) bivalent | lower hinge of IgG4 at 233-236 replaced with G (and S228P) | 381 | -51 | NB | NB | NB | NB | NB |
| 9F7_VH_IgG4_No_G(233-236) | aCD3(9F7) bivalent | lower hinge of IgG4 at 233-236 deleted (and S228P) | 382 | -56 | NB | NB | NB | NB | NB |
| Control Ab A (Lot- L2) 9F7_VH_IgG4 | aCD3(9F7) bivalent | wild type IgG4 Fc (except CH3 mutation 435R and 436F) | 383 | 17 | - | - | 140uM | - | 528 |
| Control Ab D Lot- L5) 9F7_VLx3B9_VH_IgG4_PVA | aCD3(9F7) x aCD20(3B9) | Bispecific mAb with lower hinge of IgG4 at 233-236 replaced with PVA (and S228P) | 382 | -5 | NB | NB | NB | NB | NB |
| Control Ab B (Lot-L2) 9F7_VH_IgG1 | aCD3(9F7) bivalent | wild type IgG1 Fc | 382 | 399 | - | - | 1.76uM | - | 528 |

*KDs were derived using steady state equilibrium dissociation constant

NB: No binding

FIG. 10

| mAb designation | Target arm | Construct description | hFcRn captured (RU) | mAb -5uM bound (RU) | ka | kd | KD* | t1/2 (min)* |
|---|---|---|---|---|---|---|---|---|
| 9F7_VH_IgG4 _GGG-(233-236) | aCD3(9F7) bivalent | lower hinge of IgG4 at 233-236 replaced with GGG (and S228P) | 214 | 22 | 2.42E+04 | 7.13E-02 | 2.95E-06 | 9.7 |
| 9F7_VH_IgG4 _GG--(233-236) | aCD3(9F7) bivalent | lower hinge of IgG4 at 233-236 replaced with GG (and S228P) | 190 | 11 | 8.89E+04 | 9.06E-02 | 1.02E-06 | 7.6 |
| 9F7_VH_IgG4_G---(233-236) | aCD3(9F7) bivalent | lower hinge of IgG4 at 233-236 replaced with G (and S228P) | 171 | 14 | 2.68E+04 | 7.26E-02 | 2.71E-06 | 9.5 |
| 9F7_VH_IgG4_No_G(233-236) | aCD3(9F7) bivalent | lower hinge of IgG4 at 233-236 deleted (and S228P) | 155 | 43 | 5.23E+04 | 6.97E-02 | 1.33E-06 | 9.9 |
| Control Ab A (Lot- L2) 9F7_VH_IgG4 | aCD3(9F7) bivalent | wild type IgG4 Fc (except CH3 mutation 435R and 436F) | 299 | 25 | 9.46E+04 | 1.47E-01 | 1.55E-06 | 4.7 |
| Control Ab D (Lot- L5) 9F7_VLx3B9_VH_IgG4_PVA | aCD3(9F7) bivalent | Bispecific mAb with lower hinge of IgG4 at 233-236 replaced with PVA (and S228P) | 246 | 21 | 1.91E+05 | 1.77E-01 | 9.25E-07 | 3.9 |

*KDs were derived using steady state equilibrium dissociation constant

Testing the aCD3 supernatants for binding to FcγR1 : U937 calcein killing assay

Testing the aCD3 purified mAbs for binding to FcγR1 : U937 calcein killing assay Jurkat/NFAT-Luc activation with purified aCD3 mAbs :
Fc Anchoring with HEK293/FcγRIIA Jurkat/NFAT-Luc activation with purified aCD3 mAbs :
Fc Anchoring with HEK293/FcγRIIA_Blocking with Control Ab E Jurkat/NFAT-Luc activation with purified aCD3 mAbs :
Fc Anchoring with HEK293/FcγRIIB Jurkat/NFAT-Luc activation with purified aCD3 mAbs :
Fc Anchoring with HEK293/FcγRIIB_Blocking with Control Ab E Jurkat/NFAT-Luc activation with purified aCD3 mAbs :
Coating Ab on maxisorp plates Testing the aCD20 mAbs for binding to FcγRIIIA : ADCC assay

SEQUENCE LISTING

<160> NUMBER OF SEQ ID NOS: 31

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Pro Pro Cys Pro Ala Pro Gly Gly Gly Gly Pro Ser Val Phe
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

```
Cys Pro Pro Cys Pro Ala Pro Gly Gly Gly Pro Ser Val Phe
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Cys Pro Pro Cys Pro Ala Pro Gly Gly Pro Ser Val Phe
1               5                   10


<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Cys Pro Pro Cys Pro Ala Pro Gly Pro Ser Val Phe
1               5                   10


<210> SEQ ID NO 5
<211> LENGTH: 326
<212> TYPE: PRT
<213> ORGANISM: Artificial Sequence
<220> FEATURE:
<223> OTHER INFORMATION: Synthetic

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205
```

```
Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325


<210> SEQ ID NO 6
<211> LENGTH: 325
<212> TYPE: PRT
<213> ORGANISM: Artificial Sequence
<220> FEATURE:
<223> OTHER INFORMATION: Synthetic

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Gln Glu Glu Met Thr Lys Asn Gln
225                 230                 235                 240
```

```
Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Leu Gly Lys
                325


<210> SEQ ID NO 7
<211> LENGTH: 324
<212> TYPE: PRT
<213> ORGANISM: Artificial Sequence
<220> FEATURE:
<223> OTHER INFORMATION: Synthetic

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

Gln Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Gly Leu Pro Ser Ser
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Gln Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270
```

-continued

```
Pro Val Leu Asp Ser Asp Gly Ser Phe Phe Leu Tyr Ser Arg Leu Thr
        275                 280                 285

Val Asp Lys Ser Arg Trp Gln Glu Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Leu Gly Lys
```

<210> SEQ ID NO 8
<211> LENGTH: 323
<212> TYPE: PRT
<213> ORGANISM: Artificial Sequence
<220> FEATURE:
<223> OTHER INFORMATION: Synthetic

<400> SEQUENCE: 8

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
    290                 295                 300

His Glu Ala Leu His Asn His Tyr Thr Gln Lys Ser Leu Ser Leu Ser
```

305 310 315 320

Leu Gly Lys

<210> SEQ ID NO 9
<211> LENGTH: 326
<212> TYPE: PRT
<213> ORGANISM: Artificial Sequence
<220> FEATURE:
<223> OTHER INFORMATION: Synthetic

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325
```

<210> SEQ ID NO 10

<211> LENGTH: 325
<212> TYPE: PRT
<213> ORGANISM: Artificial Sequence
<220> FEATURE:
<223> OTHER INFORMATION: Synthetic

<400> SEQUENCE: 10

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Gln Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300

Val Met His Glu Ala Leu His Asn Arg Phe Thr Gln Lys Ser Leu Ser
305                 310                 315                 320

Leu Ser Leu Gly Lys
                325
```

<210> SEQ ID NO 11
<211> LENGTH: 324
<212> TYPE: PRT
<213> ORGANISM: Artificial Sequence
<220> FEATURE:
<223> OTHER INFORMATION: Synthetic

<400> SEQUENCE: 11

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Gly Gly Pro Ser Val Phe Leu Phe Pro Pro Lys Pro Lys Asp Thr Leu
115 120 125

Met Ile Ser Arg Thr Pro Glu Val Thr Cys Val Val Val Asp Val Ser
130 135 140

Gln Glu Asp Pro Glu Val Gln Phe Asn Trp Tyr Val Asp Gly Val Glu
145 150 155 160

Val His Asn Ala Lys Thr Lys Pro Arg Glu Glu Gln Phe Asn Ser Thr
165 170 175

Tyr Arg Val Val Ser Val Leu Thr Val Leu His Gln Asp Trp Leu Asn
180 185 190

Gly Lys Glu Tyr Lys Cys Lys Val Ser Asn Lys Gly Leu Pro Ser Ser
195 200 205

Ile Glu Lys Thr Ile Ser Lys Ala Lys Gly Gln Pro Arg Glu Pro Gln
210 215 220

Val Tyr Thr Leu Pro Pro Ser Gln Glu Glu Met Thr Lys Asn Gln Val
225 230 235 240

Ser Leu Thr Cys Leu Val Lys Gly Phe Tyr Pro Ser Asp Ile Ala Val
245 250 255

Glu Trp Glu Ser Asn Gly Gln Pro Glu Asn Asn Tyr Lys Thr Thr Pro
260 265 270

Pro Val Leu Asp Ser Asp Gly Ser Phe Phe Leu Tyr Ser Arg Leu Thr
275 280 285

Val Asp Lys Ser Arg Trp Gln Glu Gly Asn Val Phe Ser Cys Ser Val
290 295 300

Met His Glu Ala Leu His Asn Arg Phe Thr Gln Lys Ser Leu Ser Leu
305 310 315 320

Ser Leu Gly Lys

<210> SEQ ID NO 12
<211> LENGTH: 323
<212> TYPE: PRT
<213> ORGANISM: Artificial Sequence
<220> FEATURE:
<223> OTHER INFORMATION: Synthetic

<400> SEQUENCE: 12

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
    290                 295                 300

His Glu Ala Leu His Asn Arg Phe Thr Gln Lys Ser Leu Ser Leu Ser
305                 310                 315                 320

Leu Gly Lys


<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
```

-continued

```
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

-continued

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 16
<211> LENGTH: 329
<212> TYPE: PRT
<213> ORGANISM: Artificial Sequence
<220> FEATURE:
<223> OTHER INFORMATION: Synthetic

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190
```

```
Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325


<210> SEQ ID NO 17
<211> LENGTH: 328
<212> TYPE: PRT
<213> ORGANISM: Artificial Sequence
<220> FEATURE:
<223> OTHER INFORMATION: Synthetic

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220
```

```
Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325


<210> SEQ ID NO 18
<211> LENGTH: 327
<212> TYPE: PRT
<213> ORGANISM: Artificial Sequence
<220> FEATURE:
<223> OTHER INFORMATION: Synthetic

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325


<210> SEQ ID NO 19
<211> LENGTH: 326
<212> TYPE: PRT
<213> ORGANISM: Artificial Sequence
<220> FEATURE:
<223> OTHER INFORMATION: Synthetic

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 20
<211> LENGTH: 329
<212> TYPE: PRT
<213> ORGANISM: Artificial Sequence
<220> FEATURE:
<223> OTHER INFORMATION: Synthetic

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320
```

Lys Ser Leu Ser Leu Ser Pro Gly Lys
325

<210> SEQ ID NO 21
<211> LENGTH: 328
<212> TYPE: PRT
<213> ORGANISM: Artificial Sequence
<220> FEATURE:
<223> OTHER INFORMATION: Synthetic

<400> SEQUENCE: 21

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Gly Gly Gly Pro Ser Val Phe Leu Phe Pro Pro Lys Pro
115 120 125

Lys Asp Thr Leu Met Ile Ser Arg Thr Pro Glu Val Thr Cys Val Val
130 135 140

Val Asp Val Ser His Glu Asp Pro Glu Val Lys Phe Asn Trp Tyr Val
145 150 155 160

Asp Gly Val Glu Val His Asn Ala Lys Thr Lys Pro Arg Glu Glu Gln
165 170 175

Tyr Asn Ser Thr Tyr Arg Val Val Ser Val Leu Thr Val Leu His Gln
180 185 190

Asp Trp Leu Asn Gly Lys Glu Tyr Lys Cys Lys Val Ser Asn Lys Ala
195 200 205

Leu Pro Ala Pro Ile Glu Lys Thr Ile Ser Lys Ala Lys Gly Gln Pro
210 215 220

Arg Glu Pro Gln Val Tyr Thr Leu Pro Pro Ser Arg Asp Glu Leu Thr
225 230 235 240

Lys Asn Gln Val Ser Leu Thr Cys Leu Val Lys Gly Phe Tyr Pro Ser
245 250 255

Asp Ile Ala Val Glu Trp Glu Ser Asn Gly Gln Pro Glu Asn Asn Tyr
260 265 270

Lys Thr Thr Pro Pro Val Leu Asp Ser Asp Gly Ser Phe Phe Leu Tyr
275 280 285

Ser Lys Leu Thr Val Asp Lys Ser Arg Trp Gln Gln Gly Asn Val Phe
290 295 300

Ser Cys Ser Val Met His Glu Ala Leu His Asn Arg Phe Thr Gln Lys
305 310 315 320

Ser Leu Ser Leu Ser Pro Gly Lys
325

<210> SEQ ID NO 22
<211> LENGTH: 327

<212> TYPE: PRT
<213> ORGANISM: Artificial Sequence
<220> FEATURE:
<223> OTHER INFORMATION: Synthetic

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn Arg Phe Thr Gln Lys Ser
305                 310                 315                 320

Leu Ser Leu Ser Pro Gly Lys
                325

<210> SEQ ID NO 23
<211> LENGTH: 326
<212> TYPE: PRT
<213> ORGANISM: Artificial Sequence
<220> FEATURE:
<223> OTHER INFORMATION: Synthetic

<400> SEQUENCE: 23

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
                325


<210> SEQ ID NO 24
<211> LENGTH: 326
<212> TYPE: PRT
<213> ORGANISM: Artificial Sequence
<220> FEATURE:
<223> OTHER INFORMATION: Synthetic

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Gly Gly Gly Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ser Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 25
<211> LENGTH: 325
<212> TYPE: PRT
<213> ORGANISM: Artificial Sequence
<220> FEATURE:
<223> OTHER INFORMATION: Synthetic

<400> SEQUENCE: 25

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Gly Gly Gly Pro Ser Val Phe Leu Phe Pro Pro Lys Pro Lys Asp Thr
115 120 125

Leu Met Ile Ser Arg Thr Pro Glu Val Thr Cys Val Val Val Asp Val
130 135 140

Ser His Glu Asp Pro Glu Val Gln Phe Asn Trp Tyr Val Asp Gly Val
145 150 155 160

Glu Val His Asn Ala Lys Thr Lys Pro Arg Glu Glu Gln Phe Asn Ser
165 170 175

Thr Phe Arg Val Val Ser Val Leu Thr Val Val His Gln Asp Trp Leu
180 185 190

Asn Gly Lys Glu Tyr Lys Cys Lys Val Ser Asn Lys Gly Leu Pro Ala
195 200 205

Pro Ile Glu Lys Thr Ile Ser Lys Thr Lys Gly Gln Pro Arg Glu Pro
210 215 220

Gln Val Tyr Thr Leu Pro Pro Ser Arg Glu Glu Met Thr Lys Asn Gln
225 230 235 240

Val Ser Leu Thr Cys Leu Val Lys Gly Phe Tyr Pro Ser Asp Ile Ser
245 250 255

Val Glu Trp Glu Ser Asn Gly Gln Pro Glu Asn Asn Tyr Lys Thr Thr
260 265 270

Pro Pro Met Leu Asp Ser Asp Gly Ser Phe Phe Leu Tyr Ser Lys Leu
275 280 285

Thr Val Asp Lys Ser Arg Trp Gln Gln Gly Asn Val Phe Ser Cys Ser
290 295 300

Val Met His Glu Ala Leu His Asn His Tyr Thr Gln Lys Ser Leu Ser
305 310 315 320

Leu Ser Pro Gly Lys
325

<210> SEQ ID NO 26
<211> LENGTH: 324
<212> TYPE: PRT
<213> ORGANISM: Artificial Sequence
<220> FEATURE:
<223> OTHER INFORMATION: Synthetic

<400> SEQUENCE: 26

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

```
Thr Val Glu Arg Lys Cys Cys Val Glu Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Phe Arg Val Val Ser Val Leu Thr Val Val His Gln Asp Trp Leu Asn
            180                 185                 190

Gly Lys Glu Tyr Lys Cys Lys Val Ser Asn Lys Gly Leu Pro Ala Pro
        195                 200                 205

Ile Glu Lys Thr Ile Ser Lys Thr Lys Gly Gln Pro Arg Glu Pro Gln
    210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ser Val
                245                 250                 255

Glu Trp Glu Ser Asn Gly Gln Pro Glu Asn Asn Tyr Lys Thr Thr Pro
            260                 265                 270

Pro Met Leu Asp Ser Asp Gly Ser Phe Phe Leu Tyr Ser Lys Leu Thr
        275                 280                 285

Val Asp Lys Ser Arg Trp Gln Gln Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Pro Gly Lys


<210> SEQ ID NO 27
<211> LENGTH: 323
<212> TYPE: PRT
<213> ORGANISM: Artificial Sequence
<220> FEATURE:
<223> OTHER INFORMATION: Synthetic

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Pro Ser Val Phe Leu Phe Pro Pro Lys Pro Lys Asp Thr Leu Met
        115                 120                 125
```

```
Ile Ser Arg Thr Pro Glu Val Thr Cys Val Val Val Asp Val Ser His
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Phe
                165                 170                 175

Arg Val Val Ser Val Leu Thr Val Val His Gln Asp Trp Leu Asn Gly
            180                 185                 190

Lys Glu Tyr Lys Cys Lys Val Ser Asn Lys Gly Leu Pro Ala Pro Ile
        195                 200                 205

Glu Lys Thr Ile Ser Lys Thr Lys Gly Gln Pro Arg Glu Pro Gln Val
    210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ser Val Glu
                245                 250                 255

Trp Glu Ser Asn Gly Gln Pro Glu Asn Asn Tyr Lys Thr Thr Pro Pro
            260                 265                 270

Met Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300

His Glu Ala Leu His Asn His Tyr Thr Gln Lys Ser Leu Ser Leu Ser
305                 310                 315                 320

Pro Gly Lys


<210> SEQ ID NO 28
<211> LENGTH: 326
<212> TYPE: PRT
<213> ORGANISM: Artificial Sequence
<220> FEATURE:
<223> OTHER INFORMATION: Synthetic

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
                325


<210> SEQ ID NO 29
<211> LENGTH: 325
<212> TYPE: PRT
<213> ORGANISM: Artificial Sequence
<220> FEATURE:
<223> OTHER INFORMATION: Synthetic

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
```

```
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ser
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn Arg Phe Thr Gln Lys Ser Leu Ser
305                 310                 315                 320

Leu Ser Pro Gly Lys
                325


<210> SEQ ID NO 30
<211> LENGTH: 324
<212> TYPE: PRT
<213> ORGANISM: Artificial Sequence
<220> FEATURE:
<223> OTHER INFORMATION: Synthetic

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Phe Arg Val Val Ser Val Leu Thr Val Val His Gln Asp Trp Leu Asn
            180                 185                 190

Gly Lys Glu Tyr Lys Cys Lys Val Ser Asn Lys Gly Leu Pro Ala Pro
        195                 200                 205

Ile Glu Lys Thr Ile Ser Lys Thr Lys Gly Gln Pro Arg Glu Pro Gln
    210                 215                 220

Val Tyr Thr Leu Pro Pro Ser Arg Glu Glu Met Thr Lys Asn Gln Val
```

-continued

```
225                 230                 235                 240

Ser Leu Thr Cys Leu Val Lys Gly Phe Tyr Pro Ser Asp Ile Ser Val
                245                 250                 255

Glu Trp Glu Ser Asn Gly Gln Pro Glu Asn Asn Tyr Lys Thr Thr Pro
            260                 265                 270

Pro Met Leu Asp Ser Asp Gly Ser Phe Phe Leu Tyr Ser Lys Leu Thr
        275                 280                 285

Val Asp Lys Ser Arg Trp Gln Gln Gly Asn Val Phe Ser Cys Ser Val
    290                 295                 300

Met His Glu Ala Leu His Asn Arg Phe Thr Gln Lys Ser Leu Ser Leu
305                 310                 315                 320

Ser Pro Gly Lys


<210> SEQ ID NO 31
<211> LENGTH: 323
<212> TYPE: PRT
<213> ORGANISM: Artificial Sequence
<220> FEATURE:
<223> OTHER INFORMATION: Synthetic

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Phe
                165                 170                 175

Arg Val Val Ser Val Leu Thr Val Val His Gln Asp Trp Leu Asn Gly
            180                 185                 190

Lys Glu Tyr Lys Cys Lys Val Ser Asn Lys Gly Leu Pro Ala Pro Ile
        195                 200                 205

Glu Lys Thr Ile Ser Lys Thr Lys Gly Gln Pro Arg Glu Pro Gln Val
    210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ser Val Glu
                245                 250                 255

Trp Glu Ser Asn Gly Gln Pro Glu Asn Asn Tyr Lys Thr Thr Pro Pro
            260                 265                 270
```

-continued

```
Met Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300

His Glu Ala Leu His Asn Arg Phe Thr Gln Lys Ser Leu Ser Leu Ser
305                 310                 315                 320

Pro Gly Lys
```

HEAVY CHAIN CONSTANT REGIONS WITH REDUCED BINDING TO FC GAMMA RECEPTORS

CROSS-REFERENCE TO RELATED APPLICATION

The present application is a non-provisional of U.S. 62/140,350 filed Mar. 30, 2015, incorporated by reference in its entirety for all purposes.

FIELD OF THE INVENTION

The present invention resides in the field of recombinant protein engineering, and relates to optimized hinge variants of immunoglobulin (Ig) proteins, methods of engineering such Ig variants and suitability of such Ig variants in biopharmaceutical practice.

REFERENCE TO A SEQUENCE LISTING

This application incorporates by reference a sequence listing submitted in computer readable form as file 10140WO01_ST25.txt, created on Mar. 28, 2016, and containing 78,815 bytes.

BACKGROUND

Antibodies of the IgG class are attractive therapeutic agents. IgGs exist as four subclasses in humans, IgG1, IgG2, IgG3, and IgG4. The heavy chain constant (CH) region of IgG comprises three domains, CH1, CH2, CH3, and a hinge linking CH1 and CH2. Although the role of each subclass appears to vary between species, the heavy chain constant domain is responsible for various biological effector functions. The human IgG subclasses mediate several cellular immune responses through their interaction with Fcγ (FcγRs), such as cell killing, phagocytosis and opsonization. Such interaction involves binding of at least functional CH2 and CH3 domains of a heavy chain constant region to an FcγR on the surface of an effector cell, such as a natural killer cell, an activated macrophage or the like. Complement-mediated lysis can also be triggered by the interaction of the Fc region with various complement components.

Effector functions are useful in some antibody therapies, such as treatment of some cancers or pathogens, in which effector function is primarily or at least partially responsible for killing cancer cells or the pathogen. However, other antibody therapies are mediated entirely or predominantly by effector-independent mechanisms, such as inhibiting a receptor-ligand interaction or agonizing a receptor. In such therapies, antibody effector functions serve little or no useful purpose but can result in undesired inflammation. In such circumstances, it may be advantageous to engineer the Fc receptor binding properties of an antibody so as to inhibit some or all of the available effector mechanisms, without substantially affecting the antibody's pharmacokinetic properties, immunogenicity and variable regions specificity and affinity.

IgG heavy chain constant regions have been mutated in various positions to test the effect of amino acids on IgG/FcγR interaction (see e.g. Canfield and Morrison, J Exp Med 73, 1483-1491 (1991); Chappel et al. JSC 268(33), 25124-31 (1993); and Armour et al., Eur. J. Immunol. 29, 2613-24 (1999)). Several amino acid residues in the hinge region and in the CH2 domain of a heavy chain constant region have been proposed as mediating binding to Fcγ receptors (see Sarmay et al., Mol Immunol 29, 633-9 (1992); Greenwood et al., Eur. J. Immunol, 23(5), 1098 (1993), Morgan et al., Immunology 86, 319 (1995), Stevenson, Chemical Immunology, 65, 57-72 (1997)). Glycosylation of a site (N297) in the CH2 domain and variations in the composition of its carbohydrates also strongly affect the IgG/FcγR interaction (Stevenson, Chemical Immunology, 65, 57-72 (1997); Siberil et al, Immunol. Ltrs. 106, 111-118 (2006)).

Alanine residues have usually been the preferred substituent for replacing a natural amino acid with an unnatural one so as to reduce function because alanine has a side chain without any functional groups. For example, the well-known technique of alanine-scanning mutagenesis systematically replaces every natural residue in a protein or protein domain with alanine to identify which natural residues contribute primarily to function. Replacing an amino acid with a functional group with alanine eliminates the functional group and its contribution to binding to any receptor, but the presence of the alanine side chain substantially preserves conformation, reducing the potential for immunogenicity or other complexities due to conformational changes. An alternative strategy replaces amino acids in the hinge region of one IgG isotype with corresponding amino acids from human IgG2 isotype so as to reduce FcγR binding without unacceptable conformational changes and consequent immunogenicity. The resulting chimeric Fc-containing antibodies include a substitution of EFLG at positions 232-236 with PVA (see WO14/121087).

SUMMARY OF THE CLAIMED INVENTION

The invention provides an immunoglobulin heavy chain comprising a constant region, wherein positions 233-236 within a hinge domain are G, G, G and unoccupied; G, G, unoccupied, and unoccupied; G, unoccupied, unoccupied, and unoccupied; or all unoccupied, with positions numbered by EU numbering. Optionally, the immunoglobulin heavy chain of claim 1 that is human IgG4 isotype. Optionally, positions 226-229 are CPPC. Optionally, the hinge domain amino acid sequence comprises CPPCPAPGGG-GPSVF (SEQ ID NO:1), CPPCPAPGG--GPSVF (SEQ ID NO:2), CPPCPAPG---GPSVF (SEQ ID NO:3), or CPPCPAP----GPSVF (SEQ ID NO:4). Optionally, the constant region has an amino acid sequences comprising SEQ ID NO:5, 6, 7 or 8 or a variant thereof having up to five insertions deletions, substitutions or insertions. Optionally, the constant region comprises SEQ ID NO: 5, 6, 7 or 8. Optionally, the constant region consists of SEQ ID NO: 5, 6, 7 or 8. Optionally, the immunoglobulin heavy chain comprises from N-terminal to C-terminal the hinge domain, a CH2 domain and a CH3 domain. Optionally, the immunoglobulin heavy chain comprises from N-terminal to C-terminal a CH1 domain, the hinge domain, a CH2 domain and a CH3 domain. Optionally, the CH1 region, if present, remainder of the hinge region, if any, CH2 region and CH3 region are the same human isotype. Optionally, the CH1 region, if present, remainder of the hinge region, if any, CH2 region and CH3 region are human IgG1. Optionally, the CH1 region, if present, remainder of the hinge region, if any, CH2 region and CH3 region are human IgG2. Optionally, the CH1 region if present, remainder of the hinge region, if any, CH2 region and CH3 region are human IgG4. Optionally, the constant region has a CH3 domain modified to reduce binding to protein A. Optionally, the immunoglobulin heavy chain of any preceding claim linked at the N-terminus to a heavy chain variable region. Optionally, the immunoglobulin heavy chain is duplexed with an immunoglobulin light chain. Optionally, the immunoglobulin heavy chain is duplexed with an immunoglobulin light chain as a heterodimer comprising two immunoglobulin heavy chains and two light chains. The two heavy chains can be the same or different. Optionally, the immunoglobulin heavy chain of any preceding claim linked at the N-terminus to a binding polypeptide. Optionally, the immunoglobulin heavy chain is linked via a linker to the binding polypeptide. Optionally, the binding polypeptide is an extracellular domain.

BRIEF DESCRIPTION OF FIGURES

FIG. 1 shows correspondence of numbering schemes in the hinge region of human IgG1, IgG2, and IgG4.

FIGS. 2-4 show the wild-type sequences of heavy chain constant regions of isotypes IgG1, IgG2, IgG3 and IgG4 with delineation into CH1, hinge, CH2 and CH3 regions.

FIGS. 6-10 show binding of various hinge-modified antibodies of human IgG4 isotype (and wild-type IgG1 isotype antibody) to human FcγRI, FcγRIIA, FcγRIIB, FcγRIIIA, and FcRn.

FIG. 12C is greatly reduced on competition with a blocking antibody, as in FIG. 12B and FIG. 12D.

DEFINITIONS

Figure 5:
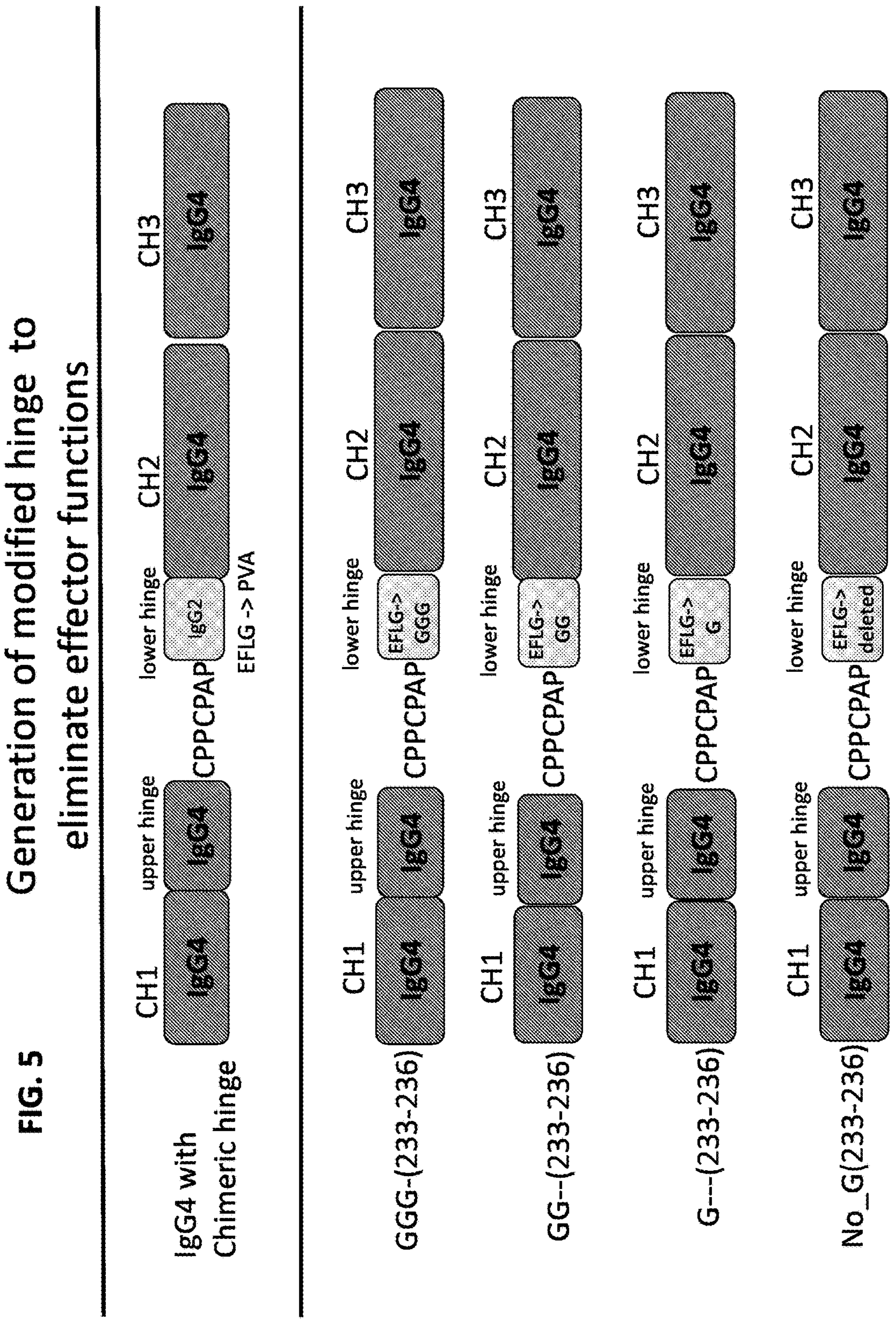
FIG. 5 is a schematic showing exemplary hinge-modified GGG-(233-236), GG--(233-236, G---(233-236) and no_G (233-236) replacement formats compared with a previously described chimeric heavy chain constant region, all of human IgG4 isotype.

Antibodies or fusion proteins are typically provided in isolated form. This means that an antibody or fusion protein is typically at least 50% w/w pure of interfering proteins and other contaminants arising from its production or purification but does not exclude the possibility that an antibody or fusion protein is combined with an excess of pharmaceutical acceptable carrier(s) or other vehicle intended to facilitate its use. Sometimes antibodies or fusion proteins are at least 60, 70, 80, 90, 95 or 99% w/w pure of interfering proteins and contaminants from production or purification. Often an antibody or fusion protein is the predominant macromolecular species remaining after its purification.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. In IgA, the heavy constant region is divided into CH1, CH2 and CH3. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding.

Light chains are classified as either kappa or lambda. Heavy chains are classified as γ, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai and Lachmann, Clin. Exp. Immunol., 79:315-321 (1990); Kostelny et al., J. Immunol., 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index is more commonly used, as is the case in this application.

An antibody or fusion protein of the invention is monospecific if all of its antigen (or ligand) binding regions have the same specificity. An antibody or fusion protein is multispecific if its antigen binding regions include at least two different specificities.

A hinge is a region of consecutive amino acid residues that connect the C-terminus of the $C_H1$ to the N-terminus of the $C_H2$ domain of an immunoglobulin. In human IgG1, IgG2 and IgG4, the hinge region runs from residue 216 to 236 by EU numbering. Residues 231-236 form a lower hinge and residues 216 to 230 form an upper and middle (or core) hinge. The demarcation between upper and middle varies by isotype. The upper and middle hinges of IgG1, IgG2 and IgG4 are 12-15 consecutive amino acids encoded by a distinct hinge exon. The lower hinge includes several N-terminal amino acids of the $C_H2$ domain (encoded by the $C_H2$ exon) (Brekke et al. Immunology Today 16(2):85-90 (1995)). IgG3 comprises a hinge region consisting of four segments: one upper segment resembling the hinge region of IgG1, and 3 segments that are identical amino acid repeats unique to IgG3.

The term "antibody" includes any form of antibody with at least one binding region including monovalent fragments, divalent tetrameric units of two heavy chains and light chains, and higher order complexes of any of these. An antibody can be mono-specific in which case all binding regions have the same specificity or multi-specific in which the binding sites have at least two specificities. Antibody fragments typically include a heavy chain variable region and a heavy chain constant region and may also include a light chain variable region. For example, an antibody fragment can include from N-terminal to C-terminal a light chain variable region, a peptide spacer, a heavy chain variable region and a heavy chain constant region of the invention. Another fragment includes a heavy chain variable region (the binding region) and a heavy chain constant region and no light chain (i.e., a Dab or nanobody). Likewise, a fusion protein includes a monomeric or dimeric fusion protein unit, or higher order complexes.

A "monoclonal antibody" refers to a preparation of antibody molecules resulting from propagation of a single clone consisting essentially of the same antibody molecules. Minor differences resulting from spontaneous mutations arising in culture or posttranslational processing may be present. A monoclonal antibody composition displays a single binding specificity and affinity for a particular epitope. Accordingly, the term "mouse or murine monoclonal antibody" refers to antibodies displaying a single binding specificity which have variable and constant regions derived from murine or mouse germline immunoglobulin sequences.

A multispecific antibody typically comprises multiple different variable domains (two in the case of bispecific antibody), wherein each variable domain is capable of specifically binding to a separate antigen or to a different epitope on the same antigen. Exemplary bispecific formats that can be used with disclosed constant regions include e.g., scFv-based bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, dual acting Fab (DAF)-IgG, and Mab2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al. 2013, J. Am. Chem. Soc. 9; 135(1):340-6 [Epub: Dec. 21, 2012]). Another exemplary multispecific format that can be used with the disclosed constant regions includes a first antigen-binding domain that specifically binds a target molecule, and a second antigen-binding domain that specifically binds an internalizing effector protein, wherein such second antigen-binding domains are capable of activating and internalizing the effector protein, e.g. a receptor. (See US 2013/0243775A1.).

Binding refers to an interaction between at least two entities, or molecular structures, such as an antibody-antigen interaction, or an Fc-containing protein to an FcγR (wherein the Fc-containing protein is an antibody, Ig, antibody-binding fragment, or Fc-fusion protein, e.g. receptor-Fc fusion). For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen or FcR as the ligand and the antibody, Ig, antibody-binding fragment, or Fc-containing protein as the analyte (or antiligand). Accordingly, an antibody or fusion protein binds to a target antigen or receptor with an affinity corresponding to a $K_D$ value that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein). There is an inverse relationship between $K_D$ and binding affinity, therefore the smaller the $K_D$ value, the higher the affinity. Thus, the term "lower affinity" relates to a lower ability to form an interaction and therefore a larger $K_D$ value.

An epitope is an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specific antigen binding peptide (in other words, the amino acid residue is within the footprint of the specific antigen binding peptide).

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody refers to antibodies having variable and constant regions derived from human germline immunoglobulin sequences. Such an antibody can be one produced by a human or human B-cells, or a transgenic mouse bearing human immunoglobulin genes, or by from a phage display, retroviral display, ribosomal display and the like (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russell et al., Nucl. Acids Research 21, 1081-1085 (1993), Hogenboom et al., Immunol. Reviews 130, 43-68 (1992), Chiswell and McCafferty, TIBTECH 10, 80-84 (1992), and U.S. Pat. No. 5,733,743). Human antibodies can include amino acid residues not encoded by human germline immunoglobulin introduced by maturation in vivo, such as by somatic mutation or gene rearrangement in vivo. Human antibodies can also include a small number of mutations (e.g., up to 10 per heavy or light chain) introduced by random or site-specific mutagenesis in vitro).

A transgenic animal for producing human antibodies refers to a non-human animal having a genome comprising one or more human heavy and/or light chain transgenes or transchromosomes (either integrated or non-integrated into the animal's natural genomic DNA) and which is capable of expressing fully human antibodies or at least antibodies with fully human variable regions. For example, a transgenic mouse can have a human light chain transgene and either a human heavy chain transgene or human heavy chain transchromosome, such that the mouse produces human antibody when immunized with target antigen and/or cells expressing the target antigen. The human heavy chain transgene may be integrated into the chromosomal DNA of the mouse, as is the case for transgenic mice, for instance HuMAb mice, such as HCo7 or HCol2 mice, or the human heavy chain transgene may be maintained extrachromosomally, as is the case for transchromosomal KM mice as described in WO02/43478. Such transgenic and transchromosomal mice (collectively referred to as "transgenic mice") are capable of producing multiple isotypes of human monoclonal antibodies to a given antigen (such as IgG, IgA, IgM, IgD and/or IgE) by undergoing V-D-J recombination and isotype switching. VELOCIMMUNE® genetically engineered mice comprise a replacement of unrearranged V(D)J gene segments at endogenous mouse loci with human V(D)J gene segments. VELOCIMMUNE® mice express chimeric antibodies having human variable domains and mouse constant domains (see, e.g., U.S. Pat. No. 7,605,237). Most other reports concern mice that express fully human antibodies from fully human transgenes in mice that have disabled endogenous immunoglobulin loci. The VELOCIMMUNE® mouse includes, in part, having a genome comprising human variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies can be isolated and operably linked to DNA encoding the human heavy chain constant regions of the invention. The DNA can then be expressed in a cell capable of expressing the fully human heavy chain of the antibody.

Several antibody effector functions are mediated at least in part by Fc receptors (FcRs), which bind the Fc region of an antibody in the constant domain (specifically, the CH2 and CH3 domain) of a typical immunoglobulin. There are a number of Fc receptors which are specific for the different classes of immunoglobulins, i.e. IgG, IgE, IgA, IgM, and IgD. The human IgG Fc receptor family is divided into three groups: FcγRI (CD64), which is capable of binding IgG with high affinity, FcγRII (CD32) and FcγRIII (CD16) both of which are low affinity receptors. Each FcγR subclass is encoded by two or three genes, and alternative RNA splicing leads to multiple transcripts, hence, a broad diversity in FcγR isoforms exists (e.g. FcγRIA (CD64; FCGR1A, Swiss Prot P12314), FcγRIB (CD64; FCRG1B), FcγRIIA (CD32; FCGR2A, Swiss Prot P12318), FcγRIIB (CD32; FCGR2B, Swiss Prot P31994), FcγRIIC (CD32; FCGR2C), FcγRIIIA (CD16a; FCGR3A, Swiss Prot P08637), and FcγRIIIB (CD16b; FCGR3B)). Furthermore, Fc receptors are expressed on a variety of cells, including, e.g., B cells, monocytes, dendritic cells, neutrophils, and certain lymphocytes. For example, U937 cells, a human monocyte cell line, express both FcγRI and FcγRIIA (see e.g., Jones, et al. J Immunol 135(5):3348-53 (1985); and Brooks, et al. J Exp Med 170:1369-85 (October 1989)).

Antibody-dependent cellular cytotoxicity or ADCC is an activity to damage a target cell when an Fcγ receptor-bearing cell (an immune cell or the like) binds to an Fc portion of a specific antibody through the Fcγ receptor, when the specific antibody has attached to a cell-surface antigen of the target cell. Thus, ADCC is a mechanism by which Fc receptor-positive effector cells can lyse target cells that have adherent antigen-specific molecule. The ADCC activity can be evaluated by for example measuring the fluorescent intensity using a fluorescent dye such as calcein AM (Wako Pure Chemical Industries, Ltd., 349-07201). When this approach is employed, the cytotoxic activity (% cell lysis) can be calculated, using the obtained values, according to the equation: $(A-C)/(B-C)\times100$, wherein A is a fluorescent value in each sample, B is an average fluorescent value of the cells lysed and released into a medium with Nonidet P-40 having a final concentration of 1%, and C is an average fluorescent value when only the medium was added.

"Antibody-dependent cellular phagocytosis" or "ADCP" relates to effector function that eliminates (or kills) a target cell by engulfing the target cell rather than inducing cytolysis. ADCP may be an important in vivo mechanism for killing tumor cells. ADCP can be measured by two-color fluorescence flow cytometry methods, for example methods utilizing, e.g. PKH2 (green fluorescent dye) and phycoerythrin-conjugated (red) monoclonal antibodies against different cell surface proteins to differentiate the test cells, thus determining phagocytic activity and rate of phagocytosis. Therapeutic strategies that selectively activate FcγRIIa relative to FcγRIIb may enhance macrophage phagocytic activity (Richards et al. 2008 Mol. Cancer Ther. 7(8):2517-27).

Complement-directed cytotoxicity or CDC refers to cytotoxic activity by the complement system. CDC activity can be measured, for example the target cells, antibody, and complement solution (such as baby rabbit complement (Cedarlane Technologies)) are incubated and are allowed to react, according to standard protocols (NIAID Manual of Tissue Typing Techniques 1979-1980, Edited by J. G. Ray, NIH Publication No. NIH-83-545.) The cytotoxic activity can be calculated in the same manner as the measurement of the ADCC activity. The cytotoxic activity can also be measured using a fluorescent dye (such as calcein) or radioactive dyes similarly to the above with respect to ADCC.

The term "subject" includes human and other mammalian subjects that receive either prophylactic or therapeutic treatment.

Compositions or methods "comprising" one or more recited elements may include other elements not specifically recited. For example, a composition that comprises antibody may contain the antibody alone or in combination with other ingredients.

DETAILED DESCRIPTION

I. General

The invention provides antibody heavy chain constant regions with a hinge region modified to reduce binding to Fcγ receptors. The modification occurs within positions 233-236 by EU numbering by replacement of natural residues by glycine(s) and/or deletion(s). The inventors unexpectedly found that such modifications in the hinge region of antibodies can usefully reduce binding of such antibodies to Fcγ receptors to a greater extent than previous modifications in this region, and particularly can reduce binding to background levels for any or all of FcγRI, FcγRIIA, FcγRIIB, and FcγRIIIA. These modified immunoglobulin constant regions can be incorporated into virtually any format of antibody or Fc fusion protein. Such antibodies or fusion proteins can be used in methods of treatment, particularly those in which the mechanisms of action of the antibody or Fc fusion protein is not primarily or at all dependent on effector functions, as is the case when an antibody inhibits a receptor-ligand interaction or agonizes a receptor.

II. Heavy Chain Constant Regions

The invention provides modified immunoglobulin heavy chain regions in which each of positions 233-236 by EU number is occupied by G or is unoccupied. Position 236 is unoccupied in canonical human IgG2 but is occupied by in other canonical human IgG isotypes. Positions 233-235 are occupied by residues other than G in all four human isotypes (see FIG. 1). Position 233 is not believed to interact directly with Fcγ receptors but was included in the mutagenesis because removing replacing the wildtype glu residue in IgG1 and IgG4 or pro residue in IgG2 in combination with the other mutations would reduce immunogenicity. In four exemplary modified constant regions, positions 233-236 are gly gly gly unoccupied, gly gly unoccupied, unoccupied; gly, unoccupied, unoccupied, unoccupied and all unoccupied (see FIG. 5). These segments can be represented as GGG-, GG--, G--- or ---- with "-" representing an unoccupied position.

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies.

Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G(233-236).

```
hIgG1
CPPCPAPELLGGPSVF

hIgG2
CPPCPAPPVA-GPSVF

hIgG4
CPSCPAPEFLGGPSVF

GGG-(233-236)
                                   (SEQ ID NO: 1)
CPPCPAPGGG-GPSVF

GG--(233-236)
                                   (SEQ ID NO: 2)
CPPCPAPGG--GPSVF

G---(233-236)
                                   (SEQ ID NO: 3)
CPPCPAPG---GPSVF

no_G(233-236)
                                   (SEQ ID NO: 4)
CPPCPAP----GPSVF
```

The modified hinge regions described above can be incorporated into a heavy chain constant region, which typically include CH2 and CH3 domains, and which may have an additional hinge segment (e.g., an upper hinge) flanking the designated region, and a CH1 region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4. A constant region is considered to be of a designated isotype if it differs from that isotype by no more than 1, 2, 3, 4, 5, 6, 7, 8, 9 or 10 substitutions, deletions or internal insertions, except however, that the CH1 domain can be omitted entirely as can the upper hinge region. CH1, CH2 and CH3 domains are considered to be of IgG1, IgG2 or IgG4 isotype if differing from the CH1, CH2 and CH3 region of the exemplified sequence by no more than 1, 2, 3, 4 or 5 substitutions, deletions or internal insertions. The remainder of a hinge outside the 226-236 region sequences presented above is considered to be of IgG1, IgG2 or IgG4 isotype if it differs from the corresponding part of the hinge region of the exemplified hinge sequences by no more than 1 or 2 substitutions, deletions or internal insertions.

Some preferred heavy chain constant regions have amino acid sequences consisting or comprising SEQ ID NO. 5, 6, 7 and 8. These heavy chain constant regions incorporate the segments SEQ ID NO:1, SEQ ID NO:2, SEQ ID:3 and SEQ ID NO:4 at residues 226-236 shown above in an otherwise-human IgG4 isotype. Other preferred constant regions differ from the designated SEQ ID NO. at up to 1, 2, 3, 4, 5, 6, 7, 8, 9 or 10 positions but retain at least GGG-, GG--, G--- or ----- at EU positions 232-236 and P at position 228 and preferably retain of residues 226-236 shown above for SEQ ID NO:1, SEQ ID NO:2, SEQ ID:3 and SEQ ID NO:4. Variations from the designated SEQ ID NOS. can represent one or several natural allotypic or isoallotypic variations, variations to increase or reduce an effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004), for which exemplary substitutions include a Gln at position 250 and/or a Leu at position 428 (EU numbering. Other variations can add or remove sites of post-translational modification, such as N-linked glycosylation at N-X-S/T motifs. Variations can also include introduction of knobs (i.e., replacement of one or more amino acids with larger amino acids) or holes (i.e., replacement of one or more amino acids with smaller amino acids) to promote formation of heterodimers between different heavy chains for production of bispecific antibodies. Exemplary substitutions to form a knob and hole pair are T336Y and Y407T respectively (Ridgeway et al., Protein Engineering vol. 9 no. 7 pp. 617-621, 1996). Variations can also include mutations that reduce protein A interaction (e.g., H435R and Y436F) in the EU numbering system. Bispecific antibodies in which one heavy chain has such a variation, and another does not, can be separated from their parental antibodies by protein-A affinity chromatography. For example, SEQ ID NOS. 9-12 are the same as SEQ ID NOS. 5-8 except for the presence of H435R and Y436F mutations. One or more residues from the C-terminus of constant regions, particularly a C-terminal lysine on the heavy chain, can be lost as a result of post-translational modification.

Other heavy chain constant regions comprise or consist of SEQ ID NOS. 16-19 and 20-23, which correspond to SEQ ID NOS. 5-8 and 9-12 respectively except that the former are of human IgG1 rather than IgG4 isotype. Other heavy chain constant regions comprise or consist of SEQ ID NOS. 24-27 and 28-31, which correspond to SEQ ID NOS. 5-8 and 9-12 respectively except the former are of human IgG2 rather than IgG4 isotype.

Other preferred constant regions differ from any of the above designated SEQ ID NO. at up to 1, 2, 3, 4, 5, 6, 7, 8, 9 or 10 positions but retain at least GGG-, GG--, G--- or at EU positions 232-236 and P at position 228 and preferably retain residues 226-236 shown above for SEQ ID NO:1, SEQ ID NO:2, SEQ ID:3 and SEQ ID NO:4 in the same manner as was discussed for IgG4 isotype constant regions.

Modified constant regions and antibodies or fusion proteins incorporating such constant regions are characterized by reduced affinity for Fcγ receptors compared with isotype matched controls (wildtype constant regions or antibodies or fusion proteins incorporating the same). Binding affinity (Ka) is preferably reduced at least 90, 95 or 99% compared with the isotype matched controls. Preferably binding affinity is reduced to background levels (i.e., same signal within experimental error as in a control reaction with an sc-Fv fragment lacking any constant region or in which an irrelevant receptor is used in place of Fcγ. Preferably, affinity is reduced to a background level or at least 90, 95 or 99% for each of human Fcγ receptors, γRI, γRIIA, γRIIB and γRIIIA.

Likewise, effector functions dependent on Fcγ receptor binding, such as ADCC or ADCP are reduced, preferably by at least 90, 95 or 99% or more preferably to background level. Such functions include cell killing or phagocytosis, B-cell activation, and release of inflammatory mediators, such as cytokines. Some such effects can be quantified by measurement of EC50, which refers to the half maximal effective concentration of an antibody which induces a response halfway between the baseline and maximum after a specified exposure time. The $EC_{50}$ essentially represents the concentration of an antibody where 50% of its maximal effect is observed. Some antibodies or fusion proteins including a modified heavy chain constant region of the invention show cytotoxicity of less than 20% cytolysis (i.e. % cytotoxicity), or less than 10%, or 5%, 4%, 3%, 2%, or even 0% or undetectable cytolysis (cytotoxicity), as measured in an in vitro or ex vivo cell killing assay compared with suitable isotype-matched control antibodies with a wildtype constant region, optionally, measured at an antibody or fusion protein concentration of 10 nM.

However, binding affinity of an antibody or fusion protein incorporating such a heavy chain constant region is preferably not substantially affected by the modified constant region. That is, the binding affinity is typically the same within experimental error or at least within a factor of 2 or 3 of a suitable control antibody with a isotype-matched wild type constant region. The same is the case for functional properties not dependent on FcγR binding, such as ability to inhibit receptor-ligand binding (e.g., EC50), or ability to agonize a receptor.

Immunogenicity of modified constant regions or antibodies or fusion proteins incorporated modified constant regions compared with isotype matched controls can be assessed in vitro from dendrocyte maturation or T-cell proliferation on challenge (Gaitonde et al., Methods Mol. Biol. 2011; 716: 267-80) or in vivo by comparing incidence of reactive antibodies against administered antibodies between populations. The immunogenicity of modified constant regions or antibodies or fusion proteins incorporating the modified constant is preferably not significantly different from the isotype matched controls or not worse than 2, 3, or 5 fold greater than the isotype matched control. Likewise, pharmacokinetic parameters such as Cmax, Caverage, area under the curve and half-life are preferably not significantly different or at least not lower by a factor of no more than 2, 3 or 5 that isotype matched controls. Such parameters can be measured in a mouse such as described in the Examples, in other animal model or a human. Substantial retention of such PK parameters provides an indication that modified constant regions or antibodies or fusion proteins incorporating them have not undergone substantial conformational changes triggering enhanced removal mechanisms.

III. Antibodies and Fusion Proteins

The modified heavy chain constant regions described above can be incorporated into antibodies or other fusion proteins. For example, for expression of a monospecific antibody, a modified heavy chain constant region is expressed fused to a heavy chain variable region and together with a light chain including a light chain variable region and a light chain constant region. The heavy and light chain bind to one another via the CH1 region of the heavy chain and light chain constant region to a form a heterodimer. Two heterodimers then pair by association of hinge, CH2 and CH3 regions of the IgG heavy chain to form a tetramer unit, as is the case for a conventional antibody. For expression of a bispecific antibody, a modified heavy constant region is expressed fused to each of two heavy chain variable regions of different target specificities. The heavy chains can each assembly with a co-expressed light chain and the heavy chain-light chain complexes form heterodimers in which both heavy chains are present. The light chain variable regions can be the same (see e.g., US 20100331527A1) or different within a unit.

The modified constant regions can be used with any type of engineered antibody including chimeric, humanized, veneered or human antibodies. The antibody can be a monoclonal antibody or a genetically engineered polyclonal antibody preparation (see U.S. Pat. No. 6,986,986).

For fusion protein proteins, a modified constant region is expressed linked to a heterologous polypeptide. A heterologous polypeptide in a fusion protein is a polypeptide not naturally linked to an immunoglobulin constant region. Such a polypeptide can be a full-length protein or any fragment thereof of sufficient length to retain specific binding to the antigen bound by the full-length protein. For example, a heterologous polypeptide can be a receptor extracellular domain or ligand thereto. The heterologous polypeptide provides a binding region at the N-terminus of the constant region and is sometimes referred to simply as a binding region. The IgG CH1 region is not typically included in the constant region for fusion proteins. The upper hinge region is sometimes omitted or replaced by a synthetic linker peptide. Exemplary receptor proteins whose extracellular domains can be combined with modified heavy chain constant regions of the invention are known in the art (see e.g. Klinkert, et al. J Neuroimmunol. 72(2): 163-8 (1997); Milligan et al., Curr Pharm. Des. 10(17): 1989-2001 (2004); and Schwache & Muller-Newen, Eur. J Cell Biol. 91 (6-7):428-34 (2012), doi: 10.1016/j.ejcb.2011.0.07.008. Epub 2011 Sep. 29).

The binding region of a fusion protein can be any of the types of binding regions used in other fusion proteins produced to date (among others).

A multi-specific antibody or fusion protein can include binding specificities for an antigen on a target (e.g., a cancer cell or pathogen) and for an antigen on an effector cell (e.g., CD3 on a T-cell). Such a multi-specific complex forms a bridge between the target cell and effector cell and promotes cytotoxic or opsonization activity of the effector cell. A multi-specific antibody or fusion protein can additionally or alternatively include binding specificities for two different antigens on the same target (e.g., a cancer cell or pathogen). Such an antibody or fusion protein can have greater selective toxicity to the target cell than an antibody or fusion protein with specificity for a single antigen. Other multi-specific antibodies or fusion proteins include binding regions for both a receptor and its ligand or counter-receptor. Such antibodies or fusion proteins can exert greater inhibition than antibodies or fusion proteins binding receptor or ligand/counterreceptor alone. Any of these specificities and others can be combined in the same multi-specific complex.

Antibodies or fusion proteins can also be chemically modified by covalent conjugation to a polymer to, for instance, further increase their circulating half-life. Exemplary polymers, and methods to attach them to peptides, are illustrated in for instance U.S. Pat. Nos. 4,766,106, 4,179,337, 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

Antibodies or fusion proteins can be radiolabeled antibody for either diagnostic or therapeutic purposes. Examples of radioisotopes include $^{3}H$, $^{14}C$, $^{15}N$, $^{35}S$, $^{90}Y$, $^{99}Tc$, and $^{125}I$, $^{131}I$, $^{186}Re$, and $^{225}Ac$. Methods for preparing radiolabeled amino acids and antibodies or fusion proteins containing them are known (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method. Other detectable markers include an enzyme, a chromophore, or a fluorescent label.

Antibodies or fusion proteins can be conjugated to a toxic agent. Toxic agents can be cytotoxic or cytostatic. Some example of toxic agents include antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

IV. Antibody Expression

Nucleic acids encoding antibody chains or fusion proteins can be made by solid state synthesis, PCR amplification of overlapping oligonucleotide fragments or site-directed mutagenesis of existing nucleic acids. Such nucleic acids are expressed in an expression vector. Vectors can be configured to encode a modified heavy chain constant region and/or human light chain constant region such that they can be expressed as fusions with inserted heavy chain and light chain variable regions or a heterologous polypeptide.

The origin of replication and expression control elements (promoter, enhancer, signal peptide and so forth) in a vector can be configured for use in different cell types, such as bacteria, yeast or other fungi, insect cells, and mammalian cells. Mammalian cells are a preferred host for expressing nucleotide segments encoding antibodies or fusion proteins of the invention (see Winnacker, From Genes to Clones, (VCH Publishers, NY, 1987)). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Preferably, an antibody or fusion protein of the invention is expressed from a monoclonal cell line.

Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Cells are transfected with one or more vectors encoding the antibody or fusion protein to be expressed. For a multi-chain antibody, the heavy and light chains can be expressed on the same or separate vectors. For expression of multi-specific complexes, the DNA encoding the components of the complexes (i.e., different antibodies or fusion proteins) can be on the same or different vectors.

Antibody or fusion protein chains are expressed, processed to remove signal peptides, assembled and secreted from host cells. Antibodies or fusion proteins can be purified from cell culture supernatants by conventional antibody purification methods. If the hybrid constant region includes an IgG portion, then the purification can include a chromatography step using protein A or protein G as the affinity reagent. Conventional antibody purification procedures, such as ion exchange, hydroxyapatite chromatograph or HPLC can also be used (see generally, Scopes, Protein Purification (Springer-Verlag, NY, 1982)).

V. Applications

Although antibodies and fusion proteins incorporating modified heavy chain constant regions of the invention can be generally used in methods of treatment or diagnosis, they are particularly useful in situations in which the mechanism of action of the antibody or fusion protein is entirely or at least predominantly independent of effector functions. Such is the case for example when the therapeutic objective is not to kill a target cell, but to inhibit or activate a cell surface molecule on its surface without triggering cytotoxicity. Another setting in which reduced binding to Fc receptors is desirable is when the antibody is bispecific, and its desired therapeutic properties arise from the different binding specificities. For example, a common usage of bispecific antibodies is to combine a tumor targeting specificity with a T cell activating specificity to trigger tumor-specific T cell killing. In this case, if the Fc portion binds to an Fc receptor, then potentially that could trigger undesirable killing of cells bearing Fc receptors by T cells, or killing of T cells by Fc receptor-bearing cells such as natural killer cells or macrophages. Another setting in which lack of effector functions can be advantageous is inhibiting aggregation of peptides that contribute to pathogenesis, such as in amyloidogenic disease. A further setting is in vivo diagnosis, in which an antibody or fusion protein is intended to bind to a target but not result in clearing the target or cells bearing the target.

VI. Targets

Antibodies or fusion proteins incorporating a modified heavy chain constant region may be directed to any number of cellular target proteins. The antibodies or fusion proteins are particularly useful for surface-bound target proteins. The desired response can be, for example, clearing of a target or cell or virus bearing the same, signal transduction through a receptor, e.g., inducing apoptosis, inhibiting a receptor binding to a ligand or counterreceptor, or internalization of an antibody or fusion protein conjugated to a toxic agent. Antibodies or fusion proteins can be made to the same targets as existing commercial antibodies or fusion proteins or can be derivatized versions of commercial antibodies or fusion proteins in which the existing constant region has been replaced by a modified constant region of the present invention.

Targets of interest include growth factor receptors (e.g., FGFR, HGFR, PDGFR, EFGR, NGFR, and VEGFR) and their ligands. Other targets are G-protein receptors and include substance K receptor, the angiotensin receptor, α and ρ adrenergic receptors, the serotonin receptors, and PAF receptor. See, e.g., Gilman, Ann. Rev. Biochem. 56:625 649 (1987). Other targets are CD (cluster of differentiation markers). Other targets include ion channels (e.g., calcium, sodium, and potassium channels), muscarinic receptors, acetylcholine receptors, GABA receptors, glutamate receptors, and dopamine receptors (see Harpold, U.S. Pat. Nos. 5,401,629 and 5,436,128). Other targets are adhesion proteins such as integrins, selectins, and immunoglobulin superfamily members (see Springer, Nature 346:425 433 (1990). Osborn, Cell 62:3 (1990); Hynes, Cell 69:11 (1992)). Other targets are cytokines, such as interleukins IL-1 through about IL-37 to-date, tumor necrosis factors, interferon, and, tumor growth factor beta, colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are amyloidogenic peptides, such as Abeta, alpha-synuclein or prion peptide. Other targets are hormones, enzymes, and intracellular and intercellular messengers, such as, adenyl cyclase, guanyl cyclase, and phospholipase C. Target molecules can be human, mammalian or bacterial. Other targets are antigens, such as proteins, glycoproteins and carbohydrates from microbial pathogens, both viral and bacterial, and tumors.

Some examples of commercial antibodies and their targets include alemtuzumab (CD52); rituximab (CD20); trastuzumab (Her/neu); nimotuzumab, cetuximab (EGFR); bevacizumab (VEGF); palivizumab (RSV); abciximab (GpIIb/IIIa); infliximab, adalimumab, certolizumab, golimumab (TNF-alpha); baciliximab, daclizumab (IL-2); omalizumab (IgE); gemtuzumab (CD33); natalizumab (VLA-4); vedolizumab (alpha4beta7); belimumab (BAFF); otelixizumab, teplizumab (CD3); ofatumumab, ocrelizumab (CD20); epratuzumab (CD22); alemtuzumumab (CD52); eculizumab (C5); canakimumab (IL-1beta); mepolizumab (IL-5); reslizumab, tocilizumab (IL-6R); ustekinumab, briakinumab (IL-12, 23). Examples of commercial fusion proteins include etanercept which binds TNF-alpha, alefacept (LFA3-Fc fusion which binds CD2), TACI-Fc fusion which binds BAFF and APRIL, abatacept (CTLA-4-Fc which binds CD80 and CD86), and romiplostim (a peptide analog of thrombopoietin fused to Fc). Any of the commercial antibodies or fusion protein can be modified to replace the existing heavy chain constant region with a modified heavy chain constant region of the invention. Alternatively, a modified heavy chain constant region can be linked to other antibodies with the same target specificity (e.g., as determined by a competition assay) as any of the above commercial antibodies or fusion proteins.

VII. Methods of Treatment and Pharmaceutical Compositions

The antibodies and fusion proteins of the invention can also be used for suppressing various undesirable immune responses including those for the same therapies in which the commercial antibodies mentioned above have been used.

One category of immune disorders treatable by antibodies or fusion proteins of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The antibodies or fusion proteins are useful, inter alia, to block alloantigen-induced immune responses in the donee.

A related use for antibodies or fusion proteins of the present invention is in modulating the immune response involved in “graft versus host” disease (GVHD). GVHD is a potentially fatal disease that occurs when immunologically competent cells are transferred to an allogeneic recipient. In this situation, the donor’s immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn’s disease, ulcerative colitis, multiple sclerosis, stiff man syndrome, rheumatoid arthritis, myasthenia gravis and lupus erythematosus. In these diseases, the body develops a cellular and/or humoral immune response against one of its own antigens leading to destruction of that antigen, and potentially crippling and/or fatal consequences. Autoimmune diseases are treated by administering one of the antibodies or fusion proteins of the invention. Other immune disorders treatable by antibodies or fusion proteins including modified constant regions of the invention include asthma, allergies, celiac disease, psoriasis, and uveitis. Celiac disease, psoriasis and uveitis are autoimmune diseases.

The antibodies or fusion proteins of the invention can be used for treating cancers in which a target antigen to which the antibody or fusion protein is expressed. The methods can be used to treat solid tumors, and particularly hematological malignancies, such as leukemia (e.g., T cell large granular lymphocyte leukemia), lymphoma (Hodgkin’s or Non-Hodgkin’s), or multiple myeloma. Solid tumors include skin (e.g., melanoma), ovarian, endometrial, bladder, breast, rectum, colon, gastric, pancreatic, lung, thymus, kidney and brain. Killing of cancer cells can result from mechanism independent of FcγR bindings, such as by induction of apoptosis, inhibition of a receptor-ligand interaction or by action of a conjugated cytotoxic moiety.

The antibodies or fusion protein can also be used for treatment of pathogenic infections, such as viral, bacterial, protozoan or fungal infection. Likewise killing can occur by mechanism independent of FcγR binding such as by inhibiting an interaction between a pathogen and a cell giving other elements of the immune system an opportunity to kill the pathogen or by action of a linked radionucleotide or toxin.

Antibodies or fusion proteins are administered in an effective regime meaning a dosage, route of administration and frequency of administration that delays the onset, reduces the severity, inhibits further deterioration, and/or ameliorates at least one sign or symptom of a disorder. If a subject is already suffering from a disorder, the regime can be referred to as a therapeutically effective regime. If the subject is at elevated risk of the disorder relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

Exemplary dosages for an antibody or fusion protein are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the subject and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody or fusion protein in the circulation, the condition of the subject and the route of administration among other factors. The frequency can be daily, weekly, monthly, quarterly, or at irregular intervals in response to changes in the subject’s condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the subject.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank’s solution, Ringer’s solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the antibodies of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine. For infections, treatment can be in combination with antibiotics, anti-virals, anti-fungal or anti-protozoan agents or the like.

VIII. Other Applications

The antibodies or fusion proteins can be used for detecting their target molecule in the context of clinical diagnosis or treatment or in research. For example, the antibodies can be used to detect a cancer-related antigen as an indication a subject is suffering from an immune mediated disorder amenable to treatment. The antibodies can also be sold as research reagents for laboratory research in detecting targets and their response to various stimuli. In such uses, antibodies or fusion proteins can be labeled with fluorescent molecules, spin-labeled molecules, enzymes or radioisotypes, and can be provided in the form of kit with all the necessary reagents to perform the assay. The antibodies or fusion protein can also be used to purify their target antigens e.g., by affinity chromatography.

Presence of labeled antibodies or fusion may be detected in vivo for diagnosis purposes. In one embodiment, diagnosis comprises: a) administering to a subject an effective amount of a labeled antibody or fusion protein; b) waiting for a time interval following administration for permitting labeled antibody or fusion protein to concentrate at sites where antigen may be detected and to allow for unbound labeled antibody to be cleared to background level; c) determining a background level; and d) detecting the labeled antibody or fusion protein in the subject, such that detection of labeled antibody above the background level is indicative that the subject has the disease or disorder, or is indicative of the severity of the disease or disorder. In accordance with such embodiment, the antibody or fusion protein is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1: Expression of Hinge-Modified Antibodies

Several of the antibodies described in the following examples are bispecific antibodies in which one arm is that of an anti-hCD3 antibody and the other arm is from an anti-hCD20 antibody as described by WO2014047231.

Antibody 1, 9F7_VH_IgG4_GGG-(233-236), was made by site-directed mutagenesis using QuikChange Lightning Site-Directed Mutagenesis Kit (Agilent Technologies, Inc.; Catalog#210518) following the manufacturer's protocol, and starting with a chimeric IgG4 CH region (which contained the modifications S228P and ELLG233-236PVA; see WO2014047231). After sequence confirmation, the coding region was moved to a parent vector using Xho1-Not1 restriction sites to avoid any mutations in the non-coding region, and subsequently generating a vector construct with the hinge-modified IgG4 CH, having the hinge modifications of SEQ ID NO:1.

The anti-CD3(9F7 VH; see "L2K" based on WO2004/106380) variable region nucleic acid sequence was amplified and introduced into the same plasmid as the hinge-modified IgG4 S228P, GGG-(233-236) and the sequence was confirmed using PCR. The final plasmid was used to produce Antibody 1 using standard cell culture methodologies for isolating antibodies.

Antibody 2, 9F7_VH_IgG4_GG--(233-236), was made analogously to Antibody 1 by using site directed mutagenesis to generate a vector construct with the hinge modified IgG4 CH with GG--(233-236) (SEQ ID NO:2). The anti-CD3(9F7 VH; see WO2004/106380) variable region nucleic acid sequence was amplified and introduced into the same plasmid using standard molecular biology methods. Ab 2 was isolated using standard methodologies.

Antibody 3, 9F7_VH_IgG4_G---(233-236), was made analogously to Antibody 1 by using site directed mutagenesis to generate a vector construct with the hinge modified IgG4 CH with G---(233-236) (SEQ ID NO:3). The anti-CD3 (9F7 VH; see WO2004/106380) variable region nucleic acid sequence was amplified and introduced into the same plasmid using standard molecular biology methods. Ab 3 was isolated using standard methodologies.

Antibody 4, 9F7_VH_IgG4_No_G(233-236), was made analogously to Antibody 1 by using site directed mutagenesis to generate a vector construct with the hinge modified IgG4 CH with No_G(233-236) (SEQ ID NO:4). The anti-CD3(9F7 VH; see WO2004/106380) variable region nucleic acid sequence was amplified and introduced into the same plasmid. Ab 4 was isolated using standard methodologies.

Antibody 5, 3B9_VH_IgG4_GGG-(233-236), was made by site-directed mutagenesis using QuikChange Lightning Site-Directed Mutagenesis Kit (Agilent Technologies, Inc.; Catalog#210518) following the manufacturer's protocol, and starting with a chimeric IgG4 CH region (which contained the modifications S228P and ELLG233-236PVA; see WO2014047231). Antibody 5 is a monospecific, bivalent anti-CD20 antibody, and the anti-CD20 variable region nucleic acid sequence (3B9 VH) was isolated using standard methodologies as described in WO2014047231.

Antibody 6, 3B9_VH_IgG4_GG--(233-236), was made analogously to Antibody 5 by using site directed mutagenesis to generate a vector construct with the hinge modified IgG4 CH with GG--(233-236) (SEQ ID NO:2). The anti-CD20 (3B9 VH; see WO2014047231) variable region nucleic acid sequence was isolated using standard methodologies.

Antibody 7, 3B9_VH_IgG4_G---(233-236), was made analogously to Antibody 5 by using site directed mutagenesis to generate a vector construct with the hinge modified IgG4 CH with G---(233-236) (SEQ ID NO:3). The anti-CD20 (3B9 VH; see WO2014047231) variable region nucleic acid sequence was isolated using standard methodologies.

Antibody 8, 3B9_VH_IgG4_No_G(233-236), was made analogously to Antibody 5 by using site directed mutagenesis to generate a vector construct with the hinge modified IgG4 CH with No_G(233-236) (SEQ ID NO:4). The anti-CD20 (3B9 VH; see WO2014047231) variable region nucleic acid sequence was isolated using standard methodologies.

Antibody 9, anti-transmembrane (TM) protein variable domains (B6H12.2, obtained from BioXCell, Cat. No. BE0019-1) were cloned in to a plasmid containing the hinge-modified IgG4 S228P, GGG-(233-236) nucleic acid, by methods similarly described for Antibody 1.

Antibody 10, B6H12.2_VH_IgG4_PVA was made according to protocols described herein, having a chimeric IgG4(S228P and ELLG233-236PVA) Fc domain.

Antibody 11, anti-FELD1_VH_IgG4_PVA antibody, is isotype matched to Antibody 10, having a chimeric IgG4 (S228P and ELLG233-236PVA) Fc domain.

Control Antibody A (Lot-L2), 9F7_VH_IgG4, is an antiCD3 (9F7 VH; see WO2004/106380) human IgG4 isotype antibody (except having a CH3* mutation 435R and 436F, designated the star mutation—see US20100331527A1).

Control Antibody B (Lot-L2), 9F7_VH_IgG1, is an antiCD3 (9F7 VH; see WO2004/106380) human IgG1 isotype antibody.

Control Antibody C: 9F7_VL×3B9_VH_IgG4, was made according to the protocols described in WO2014047231. Control Ab C is a bispecific antiCD3×anti-CD20 monoclonal antibody having a wild-type IgG4 heavy chain (except one arm has the star mutation in the CH3 region for ease of bispecific antibody isolation).

Control Antibody D (Lot-L5): 9F7_VL×3B9_VH_IgG4_PVA, was made according to the protocols described in WO2014047231. Control Ab D is a bispecific anti-CD3×anti-CD20 monoclonal antibody having a modified IgG4 heavy chain [chimeric IgG4(S228P and ELLG233-236PVA), except one heavy chain has the star mutation in the CH3 region for ease of bispecific antibody isolation].

Control Antibody E: Anti-FelD1 monoclonal antibody binds a feline antigen with no cross-reactivity to human CD20 or CD3. This IgG1 non-specific antibody control was obtained by methods described in PCT Publication No. WO2013/166236, published on Nov. 7, 2013.

Control Antibody F: is small batch (supernatant) preparation of 9F7 (anti-CD3) with the chimeric IgG4 Fc (S228P and ELLG233-236PVA) (See also WO2014047231).

Control Ab G: 9F7_VH_IgG4_PVA was made according to the protocols described in WO2014047231 (Lot#2, purified). Control Ab G is a monospecific anti-CD3 monoclonal antibody having a modified IgG4 heavy chain [chimeric IgG4(S228P and ELLG233-236PVA), except one heavy chain has the star mutation in the CH3 region for ease of bispecific antibody isolation].

Control Ab H (Lot #02-091210): 3B9_VH_IgG1 is an anti-CD20 (3B9 VH; see WO2004/106380) human IgG1 isotype antibody.

Control Ab I (Lot #01-110607): 3B9_VH_IgG4 is an anti-CD20 (3B9 VH; see WO2004/106380) human IgG4 isotype antibody.

Control Ab J (Lot # L1): 9F7_VK×3B9_VH_IgG4_PVA was made according to the protocols described in WO2014047231. Control Ab J is a bispecific anti-CD3×anti-CD20 monoclonal antibody having a modified IgG4 heavy chain [chimeric IgG4 (S228P and ELLG233-236PVA), except one heavy chain has the star mutation in the CH3 region for ease of bispecific antibody isolation].

Example 2: Loss of Affinity to Fcγ Receptors

The hinge-modified antibodies (i.e. GGG-, GG--, G--- or no-G hinge replacement; Antibodies 1-4) and various control antibodies were tested for binding affinity to Fcγ receptors by surface plasmon resonance (SPR). The controls included Control Ab D (antiCD3×antiCD20-sIgG4 (S228P and ELFG233-236PVA), Control Ab B (antiCD3, human IgG1 isotype), and Control Ab A (antiCD3, human IgG4 isotype).

Briefly SPR experiments were performed at 25° C. on a Biacore T200 instrument employing a carboxymethyl dextran-coated (CM-5) chip. A mouse monoclonal anti-penta-histidine antibody (GE Healthcare) was immobilized on the surface of the CM-5 sensor chip using standard amine-coupling chemistry. 140RU-376RU of His-tagged human or monkey FcγR proteins were captured on the anti-penta-histidine amine-coupled CM-5 chip (or in the case of FcRn, about 155-299 RU of FcRn mutant constructs were immobilized on a high density anti-myc coated Biacore chip) and stock solutions of antibodies were injected at 20 μl/min for 2.5 min over the captured proteins and serially diluted. mAb binding response was monitored and, for low affinity receptors, steady-state binding equilibrium was calculated. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(In2/(60*$k_d$). Some KDs were derived using the steady state equilibrium dissociation constant; NB=no binding observed.

An anti-CD3 antibody designated 9F7 having a heavy chain constant region including hinge segments designated SEQ ID NO:1, SEQ ID NO:2, SEQ ID:3 or SEQ ID NO:4 at residues 226-236, and of human IgG4 isotype, was tested for binding affinity to human FcγRI, RIIA, RIIB and RIII. Controls included the same antibody with wildtype IgG1 or IgG4 isotypes, and the same antibody with IgG4 isotype with a different modification of the hinge region (i.e. the hinge modification has positions 226-236 occupied by CPPCPAPPVA-, the same sequences as in human IgG2, therefore referred to as chimericFc). In the IgG4 chimeric Fc format, the remaining segments of the constant region are human IgG4. In the IgG1 chimeric Fc format, the CH1 and CH3 segments are human IgG1 and CH2 is human IgG4.

The data show binding is reduced to background levels in all of the hinge-modified Antibodies 1-4 to each of human FcγRI, IIA, IIB and III. By contrast, binding of the IgG1 and IgG4 chimeric Fc antibodies is reduced to background levels for FcγRI and FcγIII, but is still significant to FcγRIIA and RIIB. All of the hinge-modified Antibodies 1-4 maintain binding to FcRn, comparable to IgG4 and chimeric hinge IgG4 formats. See FIGS. 6-10.

Example 3: Cytotoxicity Analysis

U937 cells are a monocyte cell line expressing FcγRI and FcγRIIA. U937 cells were used as a positive killer effector control in the following cytotoxicity assay. As such, the ability of antibodies with chimeric CH regions to kill U937 cells via Fc/FcγR interactions was tested. Calcein killing assays were carried out using the following protocol: Human and cynomolgus Peripheral Blood Mononuclear Cells (PBMCs) were isolated over Ficoll-Paque (GE Healthcare Life Sciences) or via Lymphocyte-Mammal density cell separation media (Cedarlane Laboratories), respectively. The isolated PBMCs were activated over a course of several days with media containing recombinant human IL-2 (30U/ml) and T-cell activation beads (anti-CD3/CD28 for human PBMC, anti-CD2/CD3/CD28 for cynomolgus PBMC). Activated T-cells were isolated from the PBMCs by centrifugation, then resuspended in 1 ml media. The magnetized beads were removed from the T-cells. Target cells (U937) were labeled with calcein, then washed and followed by incubation (10,000 cells per well) with 15-fold serial dilutions of purified Ab/sup and immortal CD8+ human T-cells (100,000 cells/well) for 3 hr at 37 C (effector:target ratio—10:1) Following incubation plates were centrifuged and the supernatant transferred to black clear bottom plates for fluorescence analysis. Each EC50, defined as the molar concentration of antibody that induces 50% cytotoxicity, was determined using Prism (GraphPad Software, San Diego, Calif.). Values were calculated using a 4-parameter nonlinear regression analysis (FIG. 11A).

Figure 11A:
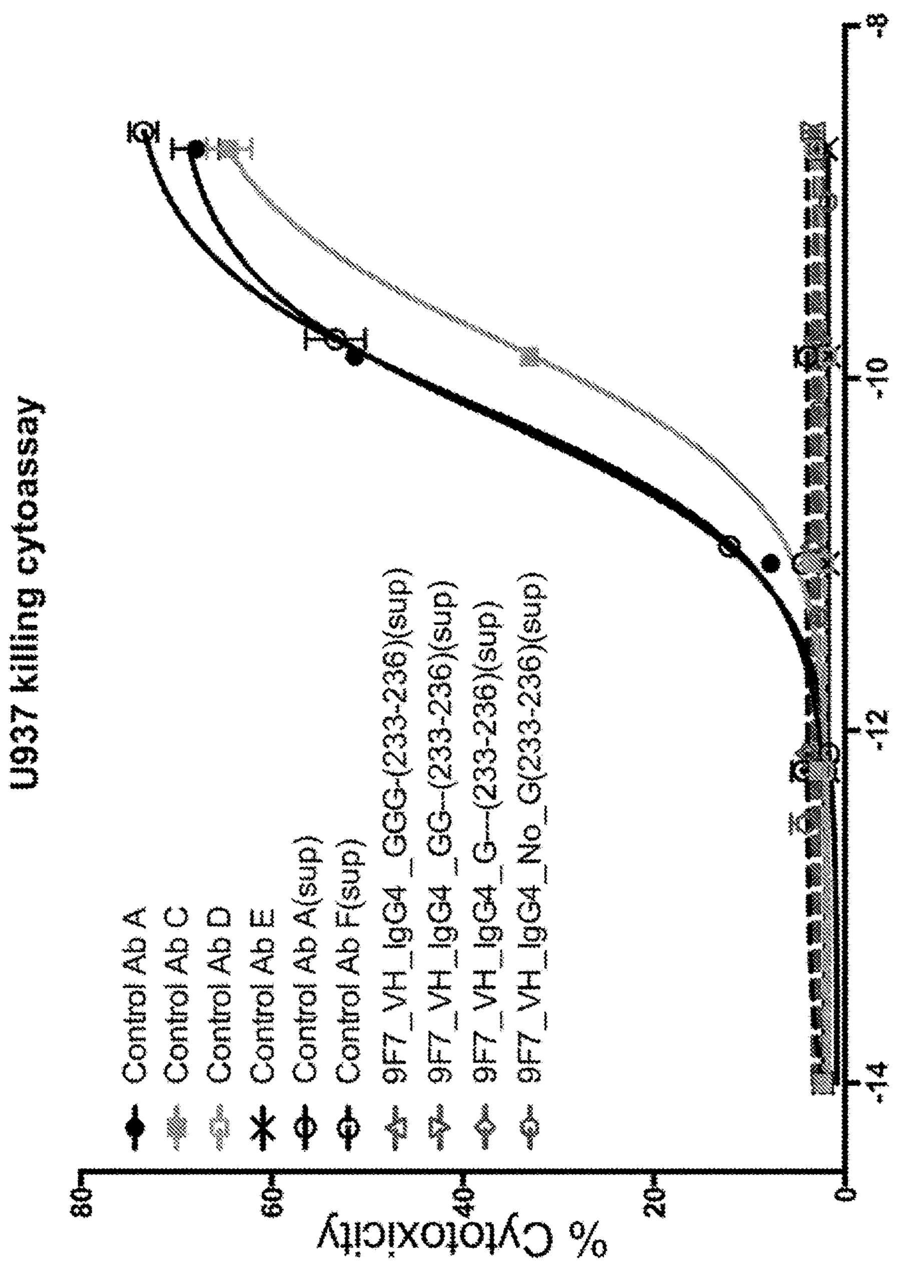
FIG. 11A shows hinge-modified antibodies (as recovered from cell culture supernatants) are unable to recruit human T-cells to lyse U937 cells, which bear FcγRI and FcγRIIA.
Figure 11B:
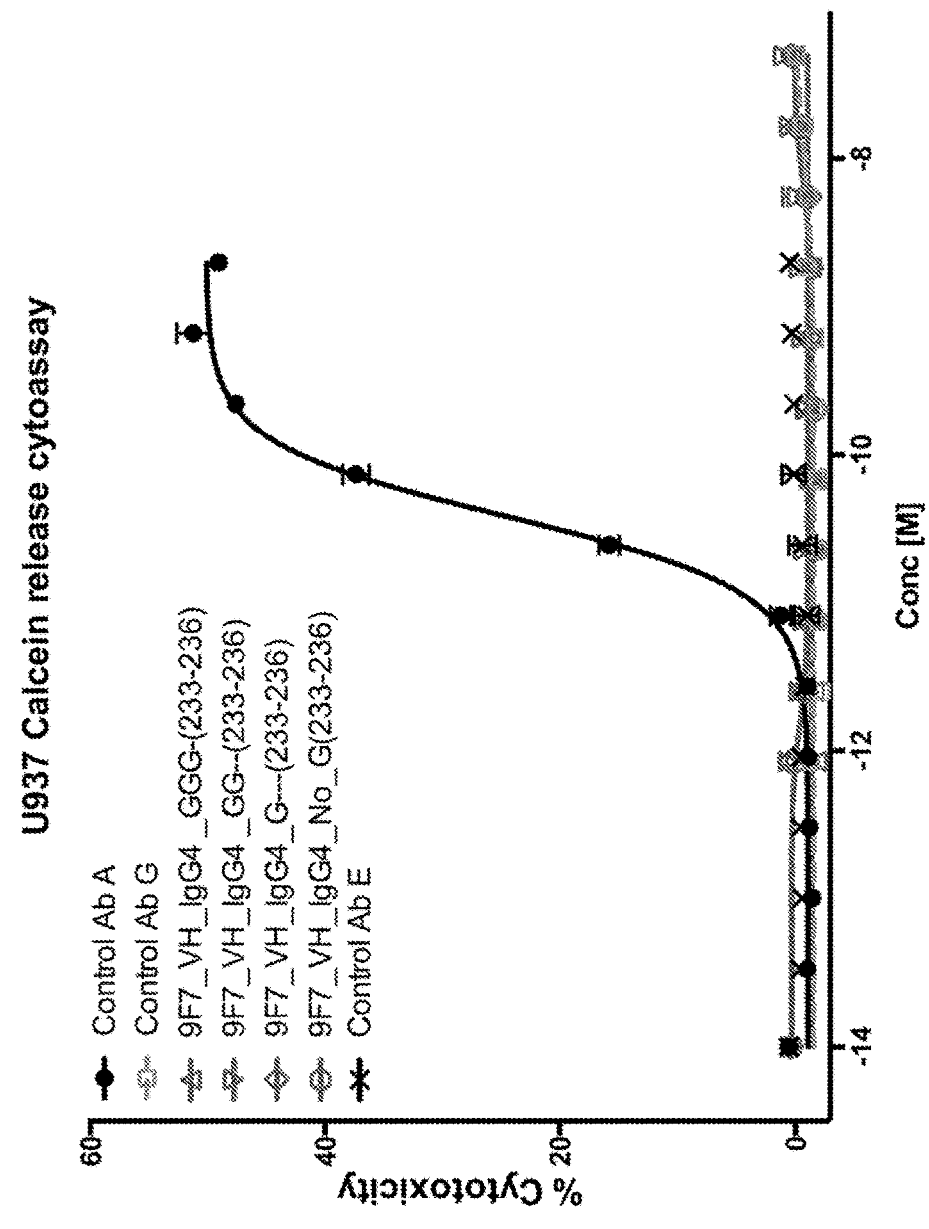
FIG. 11B also shows hinge-modified antibodies, that have been fully purified, and that are unable to recruit human T-cells to lyse U937 cells bearing FcγRI and FcγRIIA.

The above experiments were performed with crude extracts of the antibodies in cell culture supernatants (FIG. 11A). Analogous experiments were done with the same antibodies purified over standard affinity columns or using the method described in Davis et al. (see U52010/0331527) for bispecific antibodies (FIG. 11B).

The data show that all of the hinge-modified antibodies 1-4 had only background levels of cytotoxicity as was also the case for the IgG4 chimeric Fc antibody. IgG1 and IgG4 wildtype antibodies showed strong cytotoxicity due to their ability to interact with FcγRI and FcγRIIA. See FIG. 11A and FIG. 11B.

Example 4: Activation of Jurkat Cells

This example tests whether an antibody can activate Jurkat cells (T cell leukemia cell line) transformed with an NFAT-luciferase construct that acts as marker of activation. Activation requires an antibody to anchor on a HEK293 cells expressing FcγRIIA or FcγRIIB.

Figure 12A:
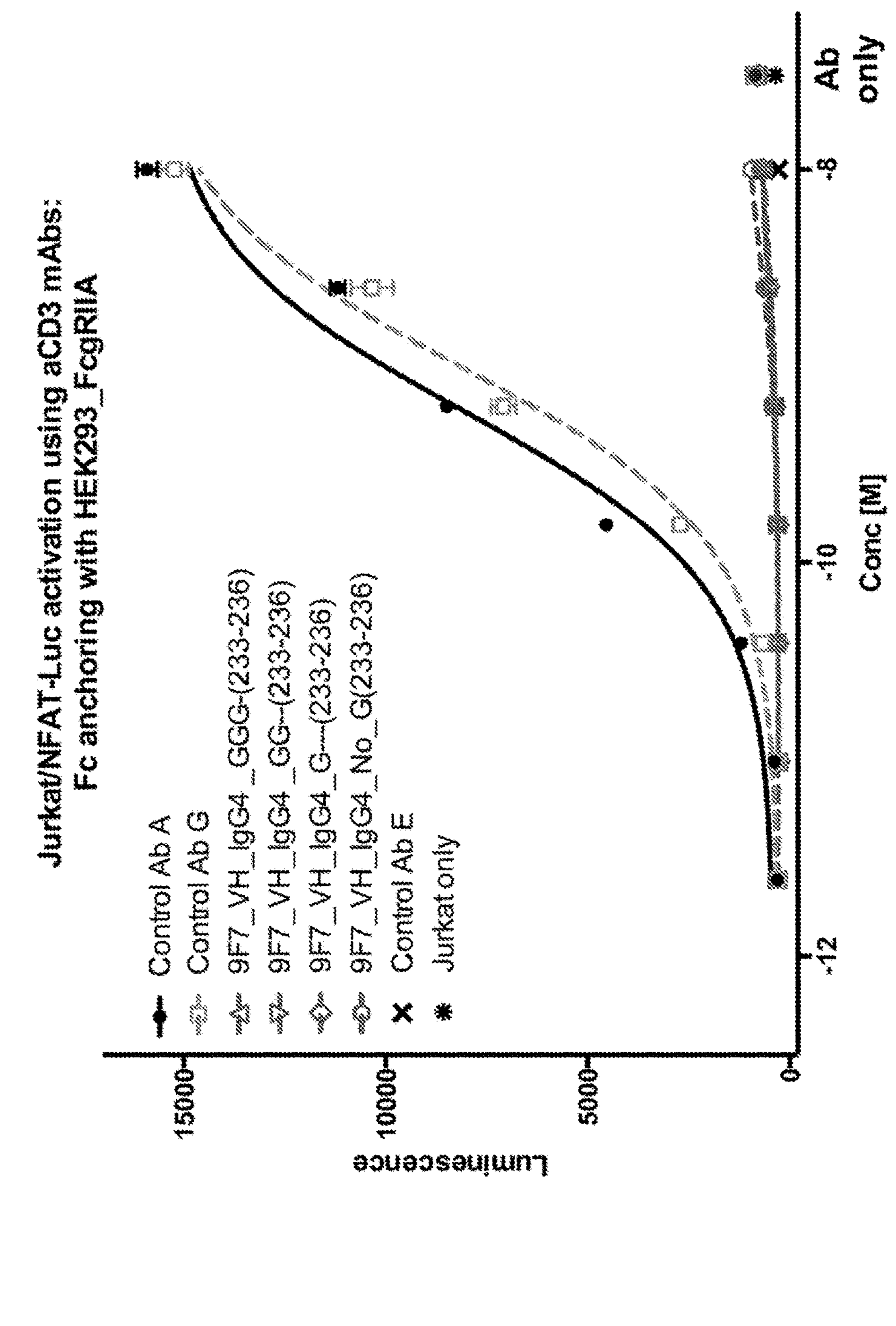
FIGS. 12A-D show that various hinge-modified antibodies show no significant activation of Jurkat cells with a luciferase marker when the activation is dependent on anchoring of the antibody to HEK cells transformed with FcγRIIA (FIG. 12A, FIG. 12B) or RIIB (FIG. 12C, FIG. 12D). The activation by the positive control antibody in FIG. 12A
Figure 12B:
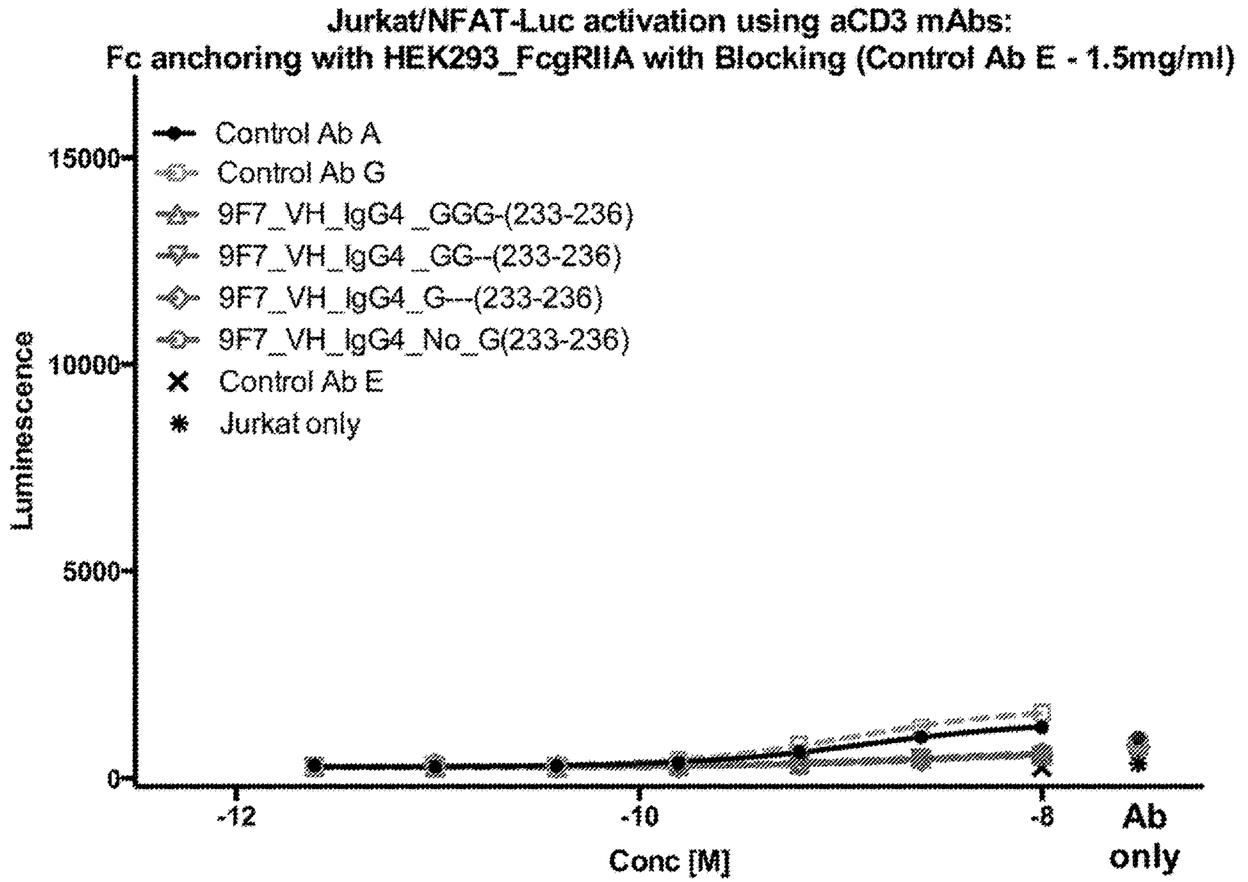
Figure 12C:
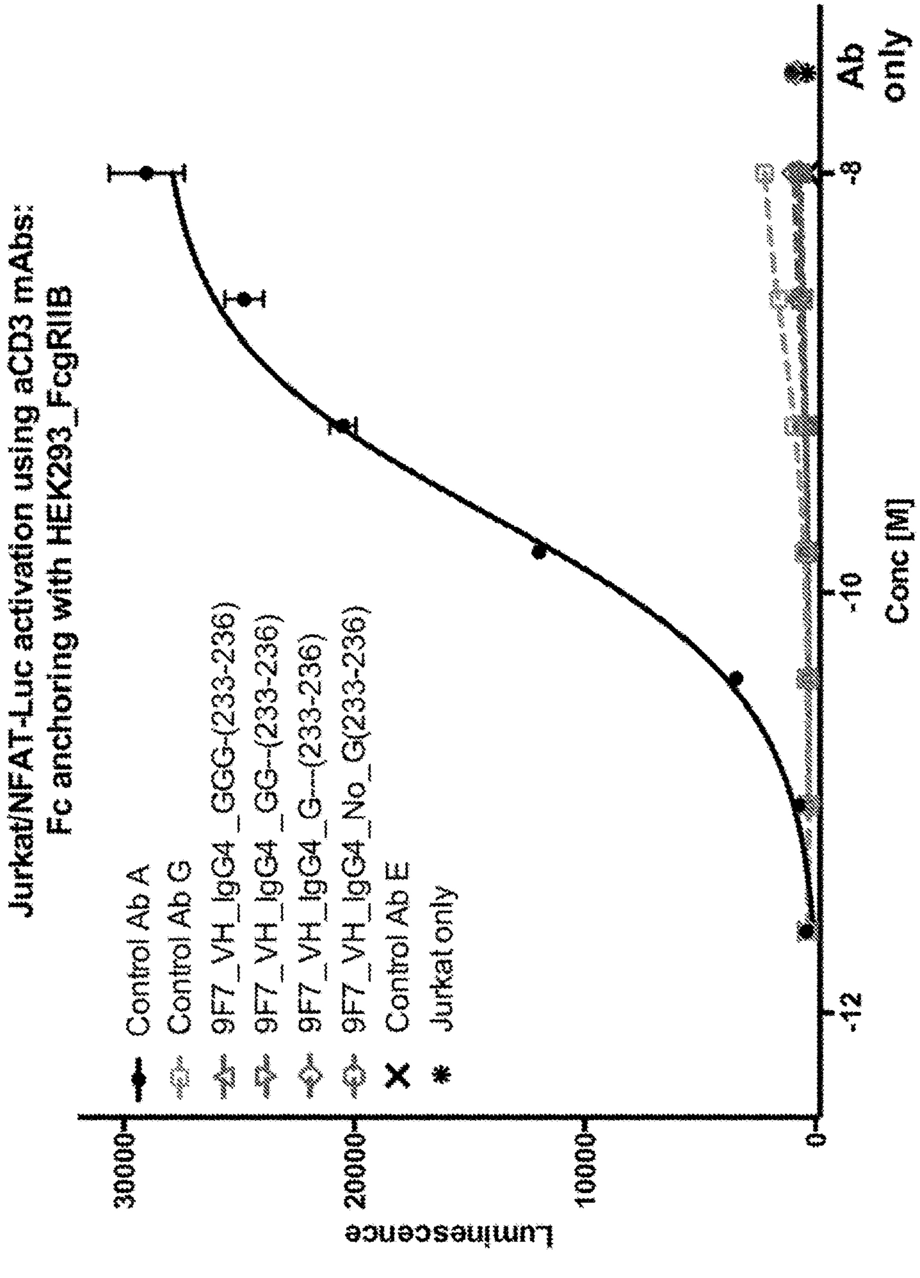
Figure 12D:
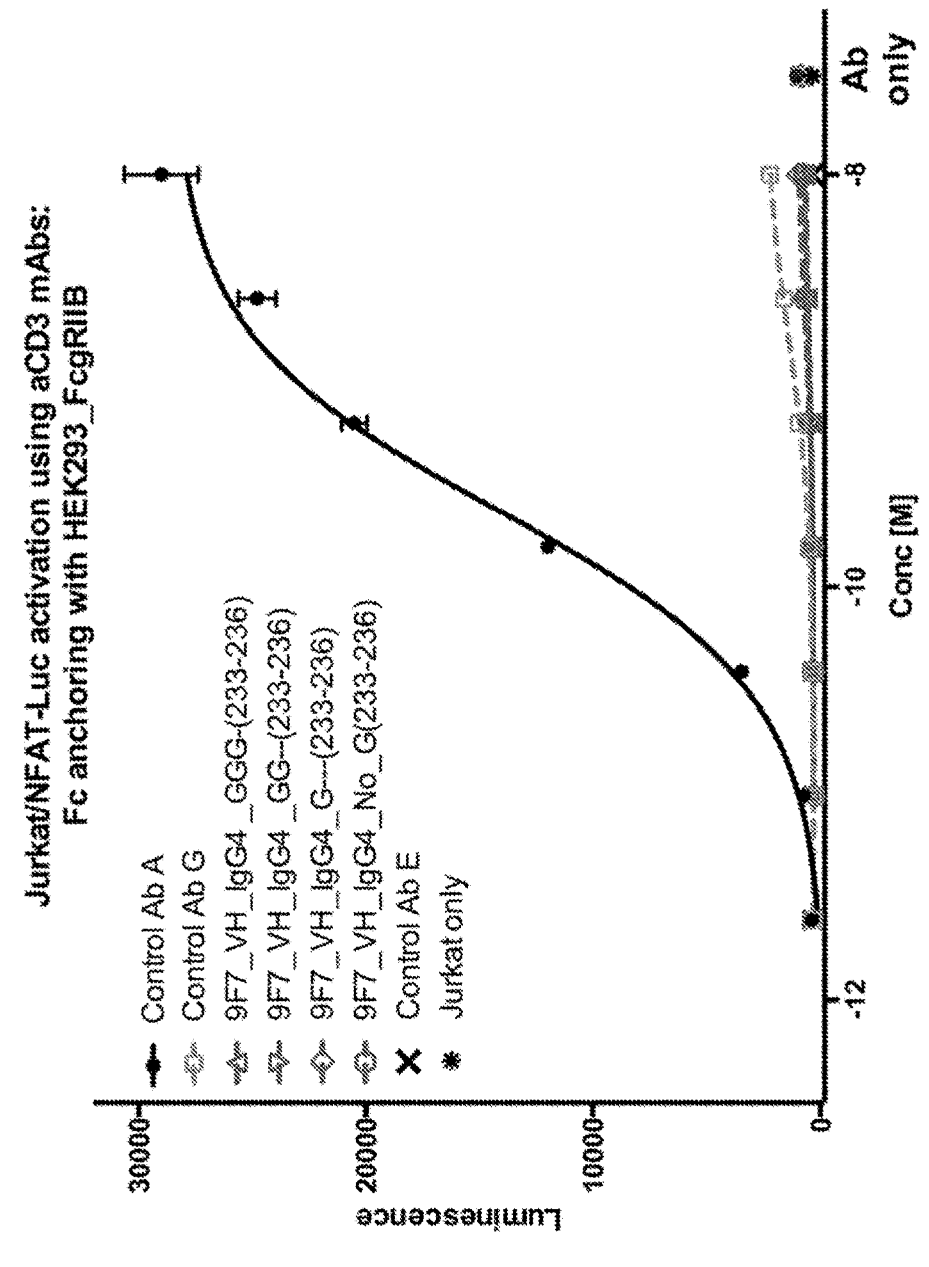

Jurkat/NFAT-Luc cells (50,000/well) were incubated with target cells (50,000/well) in the presence of serial dilutions of different antibodies with (FIG. 12B, 12D) or without (FIG. 12A, 12C) antibody to an irrelevant antigen (FelD1) (1.5 mg/ml) for 4h at 37 C. One-Glo (Promega) was added to measure luciferase activity.

The data show that all of the hinge-modified Antibodies 1-4 had only background levels of activation. See. FIGS. 12A-12D. Accordingly, all hinge-modified Antibodies 1-4 lack ability to bind to FcγRIIA or IIB on HEC cells.

A positive control antibody of wildtype human IgG4 antibody showed strong activation that was reduced to near background levels by the anti-FelD1 antibody, which competes for an anchoring site on HEK293.

Figure 13:
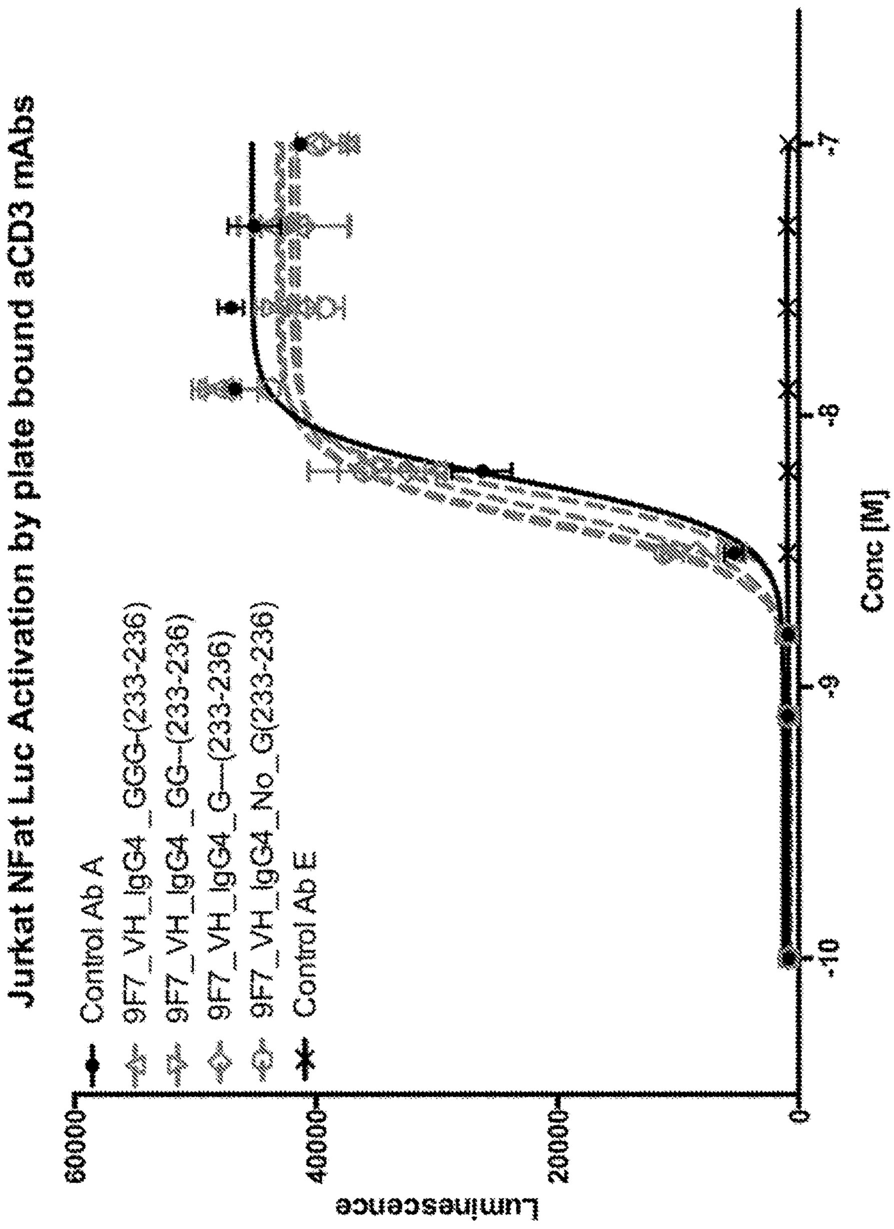
FIG. 13 shows hinge-modified antibodies activating Jurkat cells with a luciferase marker when the antibodies are anchored to a plate surface instead of by attempted binding to an FcγRIIA or RIIB receptor on the HEK cells.

To show that the lack of activation of Jurkat cells resulted from dampening the FcγR binding ability of hinge-modified antibodies rather than an impaired ability of the antibodies to bind their CD3 target, an assay was performed with the antibodies cross-linked to a plate surface. Maxisorp plates were coated with a 2-fold serial dilution of different Abs starting at 10 nM overnight at 4° C. Next day 50,000 Jurkat NFAT Luc cells were added per well and media to make up the total volume to 100 ul/well and incubate at 37° C. for 5 hours. 100 ul One-Glo (Promega) was added to measure luciferase activity. Transfer to opaque white nunc plates before reading luciferase activity. In this experiment all of the hinge-modified antibodies 1-4 showed similar activation to IgG4 isotype matched controls. See FIG. 13.

Example 5: ADCC Assay

Figure 14:
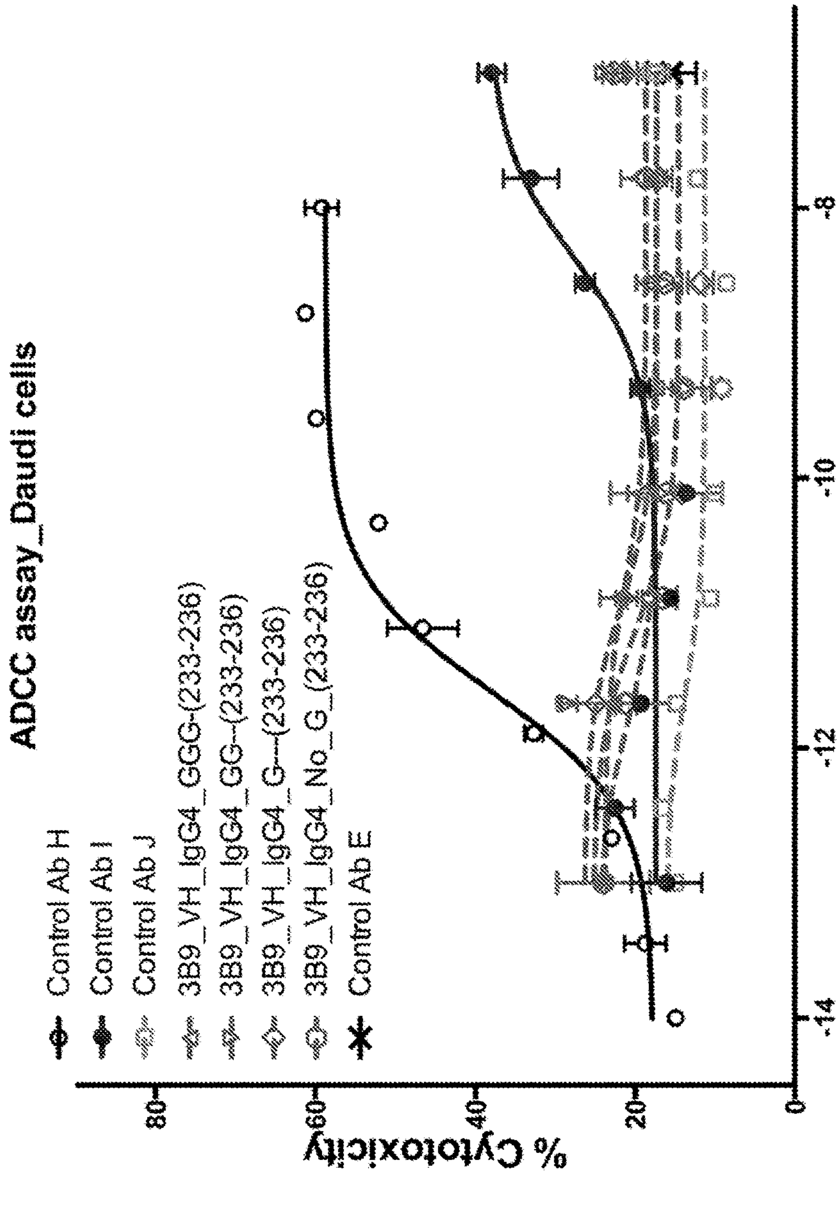
FIG. 14 shows hinge-modified antibodies having variable regions that bind CD20 display reduced antibody-dependent cellular cytotoxicity (ADCC) in the presence of NK cells cells engineered to express the higher affinity V allele of FcγRIIIa and CD20-expressing Daudi cells.

In this assay, the hinge-modified antibodies have variable regions (3B9_VH) that bind the cell surface target antigen CD20 (Antibodies 5 through 8, described above). CD20 positive target cells (Daudi) were labeled with calcein, then washed and followed by incubation (10,000 cells per well) with 6-fold serial dilutions of purified antibody and NK92_CD16V cells (NK92 cells engineered to express the higher affinity V allele of FcγRIIIa at 50,000 cells/well) for 4 hr at 37 C (effector:target ratio—5:1). Target cell lysis was determined by measuring the calcein fluorescence in the supernatant. Percent cytotoxicity and EC50 were calculated analogously to that described in Example 3. FIG. 14 shows the hinge-modified antibodies do not mediate ADCC activity (FIG. 14) against Daudi cells.

Example 6: PK Assessment of Anti-TM Monoclonal Antibody with Modified Hinge

Antibodies having variable domains that bind to a multipass transmembrane (TM) protein widely expressed in normal tissues and upregulated in various cancers were produced using well known techniques (see U.S. Pat. No. 5,057,604; WO 2011/143624; and WO 97/27873).

Assessment of the Pharmacokinetic (PK) Clearance Rate: anti-TM antibody having a modified hinge (Antibody 9) and a chimeric IgG4 Fc (Antibody 10), as well as an isotype control with chimeric IgG4 Fc (Antibody 11) were assessed in C57BL/6 Wild-Type (WT) mice. For each anti-TM mAb or isotype control, cohorts of three mice were given a subcutaneous (s.c.) dose at 1 mg/kg. Mice were bled prior to the dosing and the serum samples were designated as a pre-bleed or zero time point. All mice were bled at 6 hours, 1, 3, 7, 10 and 14 days post injection for PK analysis. Serum fractions from the bleeds were separated and frozen at −80° C. until analysis was conducted.

Determination of Total Drug Level in Sera by ELISA:

Circulating anti-TM antibody levels were determined by total human antibody analysis using an ELISA immunoassay. Briefly, a goat anti-human IgG polyclonal antibody (Jackson ImmunoResearch, #109-005-098) at 1 μg/ml in PBS was immobilized on 96-well plates overnight and the plates were blocked with 5% BSA. The drug containing serum samples in six-dose serial dilutions and the reference standards of the respective antibodies in 12-dose serial dilutions were transferred to the prepared plates and incubated for one hour. The plate-bound anti-TM antibodies were then detected using a goat anti-human IgG polyclonal antibody conjugated with horseradish peroxidase (Jackson ImmunoResearch, #109-035-098). The plates were developed with TMB substrate (BD Pharmingen, #51-2606KC, #15-2607KC) according to manufacturer's recommend protocol and signals of optical density (OD) at 450 nm were recorded using a Perkin Elmer Victor X4 Multimode Plate Reader. The anti-TM antibody concentrations in the sera were calculated based on the reference standard calibration curve generated using GraphPad Prism software.

C57BL/6 WT mice were given a single s.c. dose of 1 mg/kg of Antibody 9, Antibody 10 or Isotype control (Ab 11). Concentrations of total antibody were determined at 6 time points over a 14-day time period. The total anti-TM antibody concentrations for each antibody are summarized in Table 1.

TABLE 1

Serum Antibody Concentrations (Days 0, 0.25, 1, 3, 7, and 14)

| Antibody | Time (d) | Total mAb concentration in mouse serum | |
|---|---|---|---|
| | | Mean (μg/mL) | +/−SD |
| Antibody 9 | 0 | ND | ND |
| Antibody 9 | 0.25 | 10 | 0.8 |
| Antibody 9 | 1 | 13.3 | 0.8 |
| Antibody 9 | 3 | 10.6 | 0.7 |
| Antibody 9 | 7 | 8.6 | 1 |
| Antibody 9 | 14 | 5.3 | 0.4 |
| Antibody 9 | 0 | ND | ND |
| Antibody 10 | 0.25 | 11.2 | 1.5 |
| Antibody 10 | 1 | 14.4 | 0.9 |
| Antibody 10 | 3 | 11.0 | 1.6 |
| Antibody 10 | 7 | 9.8 | 0.9 |
| Antibody 10 | 14 | 6.4 | 0.5 |
| Antibody 11 | 0 | ND | ND |
| Antibody 11 | 0.25 | 10.1 | 0.9 |
| Antibody 11 | 1 | 12.0 | 0.4 |
| Antibody 11 | 3 | 10 | 0.6 |
| Antibody 11 | 7 | 9 | 0.8 |
| Antibody 11 | 14 | 5.1 | 0.2 |

Time = Time in days post single-dose injection;
Day = Day of study;
SD = Standard deviation;
ND = Not detected The mean concentration versus time profiles show that all three antibodies achieved a maximum serum concentration ($C_{max}$) on day 1. Antibody 9, Antibody 10 and Isotype control had comparable $C_{max}$ values of 13, 14 and 12 μg/mL, respectively. All three antibodies exhibited a linear elimination with overlapping PK profiles. These PK profiles are similar to those seen in previous studies for IgG1 and IgG4(S228P) isotype controls (data not shown). At day 14, Antibody 9 and isotype control has average drug levels around 5 μg/mL while Antibody 10 had average drug levels around 6 μg/mL.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

SEQUENCE LISTING

GGG-(233-236)
SEQ ID NO: 1
PPCPAPGGG-GPSVF

GG--(233-236)
SEQ ID NO: 2
CPPCPAPGG--GPSVF

G---(233-236)
SEQ ID NO: 3
CPPCPAPG---GPSVF

No_G-(233-236)
SEQ ID NO: 4
CPPCPAP----GPSVF

IgG4 _GGG-(233-236)
SEQ ID NO: 5
ASTKGPSVFP LAPCSRSTSE STAALGCLVK DYFPEPVTVS WNSGALTSGV HTFPAVLQSS GLYSLSSVVT

VPSSSLGTKT YTCNVDHKPS NTKVDKRVES KYGPPCPPCP APGGGGPSVFLFPPKPKDT LMISRTPEVT

CVVVDVSQED PEVQFNWYVD GVEVHNAKTK PREEQFNSTYRVVSVLTVLH QDWLNGKEYK CKVSNKGLPS

-continued

| SEQUENCE LISTING |
|---|
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNHYTQKS LSLSLGK |
| IgG4 _GG--(233-236) |
| SEQ ID NO: 6 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGGGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNHYTQKS LSLSLGK |
| IgG4 _G---(233-236) |
| SEQ ID NO: 7 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNHYTQKS LSLSLGK |
| IgG4 _No_G-(233-236) |
| SEQ ID NO: 8 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNHYTQKS LSLSLGK |
| IgG4* _GGG-(233-236) |
| SEQ ID NO: 9 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGGGGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNRFTQKS LSLSLGK |
| IgG4* _GG--(233-236) |
| SEQ ID NO: 10 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGGGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNRFTQKS LSLSLGK |
| IgG4* _G---(233-236) |
| SEQ ID NO: 11 |
| ASTKGPSVFP LAPCSRSTSE STAALGCLVK DYFPEPVTVS WNSGALTSGV HTFPAVLQSS GLYSLSSVVT |
| VPSSSLGTKT YTCNVDHKPS NTKVDKRVES KYGPPCPPCP APGGPSVFLFPPKPKDT LMISRTPEVT |
| CVVVDVSQED PEVQFNWYVD GVEVHNAKTK PREEQFNSTYRVVSVLTVLH QDWLNGKEYK CKVSNKGLPS |
| SIEKTISKAK GQPREPQVYT LPPSQEEMTK NQVSLTCLVK GFYPSDIAVE WESNGQPENN YKTTPPVLDS |
| DGSFFLYSRL TVDKSRWQEGNVFSCSVMHE ALHNRFTQKS LSLSLGK |

-continued

SEQUENCE LISTING

IgG4* _No_G-(233-236)

SEQ ID NO: 12

ASTKGPSVFP LAPCSRSTSE STAALGCLVK DYFPEPVTVS WNSGALTSGV HTFPAVLQSS GLYSLSSVVT

VPSSSLGTKT YTCNVDHKPS NTKVDKRVES KYGPPCPPCP APGPSVFLFPPKPKDT LMISRTPEVT

CVVVDVSQED PEVQFNWYVD GVEVHNAKTK PREEQFNSTYRVVSVLTVLH QDWLNGKEYK CKVSNKGLPS

SIEKTISKAK GQPREPQVYT LPPSQEEMTK NQVSLTCLVK GFYPSDIAVE WESNGQPENN YKTTPPVLDS

DGSFFLYSRL TVDKSRWQEGNVFSCSVMHE ALHNRFTQKS LSLSLGK

SEQ ID NOS. 13-15 are wildtype human IgG1, IgG2 and IgG4 as shown in FIGS. 2-4.

IgG1 GGG

SEQ ID NO: 16

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGGGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

IgG1 GG

SEQ ID NO: 17

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

IgG1 G

SEQ ID NO: 18

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

IgG1 no G

SEQ ID NO: 19

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APG PSVFLFPPKP KDTLMISRTP EVTCVVVDVS

HEDPEVKFNW YVDGVEVHNA KTKPREEQYN STYRVVSVLT VLHQDWLNGK

-continued

SEQUENCE LISTING

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

IgG1* GGG

SEQ ID NO: 20

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGGGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNRFT QKSLSLSPGK

IgG1* GG

SEQ ID NO: 21

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNRFT QKSLSLSPGK

IgG1* G

SEQ ID NO: 22

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNRFT QKSLSLSPGK

IgG1* no G

SEQ ID NO: 23

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCPPCP APG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNRFT QKSLSLSPGK

IgG2 GGG
SEQ ID NO: 24:
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGGGPSVF LFPPKPKDTL MISRTPEVTC VVVDVSHEDP

-continued

| SEQUENCE LISTING |
| --- |

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK

IgG2 GG
SEQ ID NO: 25:
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK

IgG2 G

SEQ ID NO: 26

ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK

IgG2 No G

SEQ ID NO: 27

ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK

IgG2* GGG
SEQ ID NO: 28:
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGGGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNRFTQKSL SLSPGK

-continued

SEQUENCE LISTING

IgG2* GG
SEQ ID NO: 29:
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNRFTQKSL SLSPGK

IgG2* G
SEQ ID NO: 30
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNRFTQKSL SLSPGK

IgG2* No G
SEQ ID NO: 31
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNRFTQKSL SLSPGK

What is claimed is:

1. An immunoglobulin heavy chain comprising a constant region, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

2. The immunoglobulin heavy chain of claim 1 that is human IgG4 isotype.

3. The immunoglobulin heavy chain of claim 1, wherein amino acid positions 226-229 are CPPC.

4. The immunoglobulin heavy chain of claim 3, wherein the hinge domain amino acid sequence comprises CPPC-PAPGGG-GPSVF (SEQ ID NO:1), CPPCPAPGG--GPSVF (SEQ ID NO:2), CPPCPAPG---GPSVF (SEQ ID NO:3), or CPPCPAP----GPSVF (SEQ ID NO:4).

5. The immunoglobulin heavy chain of claim 1, wherein the constant region has an amino acid sequence comprising SEQ ID NO:5, 6, 7 or 8 or a variant thereof having up to five insertions deletions, substitutions or insertions.

6. The immunoglobulin heavy chain of claim 1, wherein the constant region comprises SEQ ID NO: 5, 6, 7 or 8.

7. The immunoglobulin heavy chain of claim 1, wherein the constant region consists of SEQ ID NO: 5, 6, 7 or 8.

8. The immunoglobulin heavy chain of claim 1 comprising from N-terminal to C-terminal, amino acid positions 233-236 of the hinge domain, a CH2 domain and a CH3 domain.

9. The immunoglobulin heavy chain of claim 1, comprising from N-terminal to C-terminal, a CH1 domain, the hinge domain, a CH2 domain and a CH3 domain.

10. The immunoglobulin heavy chain of claim 9, wherein the CH1 domain, remainder of the hinge domain, if any, CH2 domain and CH3 domain are the same human isotype.

11. The immunoglobulin heavy chain of claim 9, wherein the CH1 domain, remainder of the hinge domain, if any, CH2 domain and CH3 domain are human IgG1.

12. The immunoglobulin heavy chain of claim 9, wherein the CH1 domain, remainder of the hinge domain, if any, CH2 domain and CH3 domain are human IgG2.

13. The immunoglobulin heavy chain of claim 9, wherein the CH1 domain, remainder of the hinge domain, if any, CH2 domain and CH3 domain are human IgG4.

14. The immunoglobulin heavy chain of claim 1, wherein the constant region has a CH3 domain modified to reduce binding to protein A.

15. The immunoglobulin heavy chain of any one of claim 1, 8 or 9, linked at the N-terminus to a heavy chain variable region.

16. The immunoglobulin heavy chain of claim 15 duplexed with an immunoglobulin light chain.

17. The immunoglobulin heavy chain of claim 15 duplexed with an immunoglobulin light chain as a heterodimer comprising two immunoglobulin heavy chains and two light chains.

18. The immunoglobulin of claim 17, wherein the two heavy chains are the same.

19. The immunoglobulin of claim 17, wherein the two heavy chains are different.

20. The immunoglobulin heavy chain of claim 1, linked at the N-terminus to a binding polypeptide.

21. The immunoglobulin heavy chain of claim 20 linked via a linker to the binding polypeptide.

22. The immunoglobulin heavy chain of claim 20, wherein the binding polypeptide is an extracellular domain.

23. The immunoglobulin heavy chain of claim 8, wherein the remainder of the hinge domain, if any, CH2 domain and CH3 domain are each selected from the group consisting of human IgG1, human IgG2, human IgG3, and human IgG4.

24. The immunoglobulin heavy chain of claim 9, wherein the CH1 domain, remainder of the hinge domain, if any, CH2 domain and CH3 domain are each selected from the group consisting of human IgG1, human IgG2, human IgG3, and human IgG4.

* * * * *